US008341015B2

(12) United States Patent
Harrell

(10) Patent No.: US 8,341,015 B2
(45) Date of Patent: Dec. 25, 2012

(54) VIRTUAL SAMPLE CABINET SYSTEM AND METHOD FOR PRESCRIPTION DRUG MARKETING

(76) Inventor: David A. Harrell, Shelby Township, MI (US)

( * ) Notice: Subject to any disclaimer, the term of this patent is extended or adjusted under 35 U.S.C. 154(b) by 0 days.

(21) Appl. No.: 12/655,558

(22) Filed: Dec. 31, 2009

(65) Prior Publication Data

US 2011/0313828 A1    Dec. 22, 2011

Related U.S. Application Data

(60) Provisional application No. 61/273,960, filed on Aug. 11, 2009, provisional application No. 61/277,161, filed on Sep. 21, 2009.

(51) Int. Cl.
*G06Q 30/00* (2012.01)
(52) U.S. Cl. ..................................... 705/14.11
(58) Field of Classification Search ............ 705/14
See application file for complete search history.

(56) References Cited

U.S. PATENT DOCUMENTS

| | | | |
|---|---|---|---|
| 5,628,530 A | 5/1997 | Thornton | |
| 5,737,539 A | 4/1998 | Edelson et al. | |
| 5,803,498 A | 9/1998 | Tung et al. | |
| 5,883,370 A | 3/1999 | Walker et al. | |
| 6,735,497 B2 | 5/2004 | Wallace et al. | |
| 6,952,681 B2 | 10/2005 | McQuade et al. | |
| 7,493,263 B2 | 2/2009 | Helmus et al. | |
| 8,082,173 B2 | 12/2011 | Kost et al. | |
| 2002/0013787 A1 | 1/2002 | Pollard et al. | |
| 2002/0111832 A1* | 8/2002 | Judge | 705/3 |
| 2003/0212577 A1 | 11/2003 | Nichtberger | |
| 2003/0216974 A1 | 11/2003 | Browne | |

* cited by examiner

*Primary Examiner* — John G. Weiss
*Assistant Examiner* — Darnell Pouncil
(74) *Attorney, Agent, or Firm* — John R. Benefiel

(57) ABSTRACT

A method is provided which provides functionality for doctors and staff to remotely electronically download a "virtual sample cabinet" software program from a central server onto their desktop computers or mobile technology devices to allow them to centrally search, review product information and insurance coverage, print or electronically send prescription drug sample vouchers and co-pay savings coupons to selected pharmacies. This eliminates the need for physician offices to manage and house physical drug samples, as well as offers a more convenient and efficient way to allocate, dispense and monitor needed drug samples and coupons for savings to their patients.

Additionally, the method helps patients to enroll into further savings on refills for their on-going medications through automatically scheduled coupons that are emailed (or mailed) to the patients thereby promoting more affordable compliance to their prescribed therapies.

A computer program system, which incorporates this method, increases effectiveness of prescription drug promotions over conventional means —while increasing productivity of providers and affordability to patients. All reporting by physician offices, affiliate groups, drug manufacturers and other participating parties can be accessed through the website administration login based on capture of redemption of each patient coupon or voucher through a network of reporting pharmacies.

2 Claims, 22 Drawing Sheets

| Prior Art Systems | | SampleMD Systems |
|---|---|---|
| Drug Company Manufactures Physical Sample/vouchers & Packaging | 1 | Eliminates this Requirement |
| Drug Company Ships Physical Samples/Vouchers to their Sales Representatives for Distribution | 2 | Eliminates this Requirement |
| Drug Rep Supplies Healthcare Provider (HCP) with Rx Physical Drug Samples & Discount Vouchers to Store in Office Sample Cabinet | 3 | Eliminates this Requirement |
| HCP Required to Login all Physical Samples by ID # on Box | 4 | Eliminates this Requirement |
| HCP Treats Patient | 5 | HCP Treats Patient |
| HCP Searches Physical Inventory in Sample Cabinet of Appropriate Rx Samples/Vouchers | 6 | HCP goes to SampleMD Downloaded Right on Desktop/Mobile to Search & Select Available Sample/Co-pay Offers |
| HCP has to Lookup Patient's Insurance Information to see what Level of Drug Reimbursement | 7 | At Same Time, HCP can review Insurance Coverage Information by Selecting Patient's Insurance |
| HCP Required to Login all Physical Samples by ID # on box and Writes Prescription. | 8 | Eliminates this Requirement. HCP Prints out for Patient or e-sends Sample Voucher/Rx to Selected Pharmacy |
| If Voucher, Patient goes to Pharmacy to Redeem. If Physical Sample, do not go to Pharmacy. | 9 | Patient goes to Pharmacy to Redeem their Sample Voucher or Co-pay Coupon. |
| Once Physical Samples run out, Patient Required to go to Pharmacy and Pay Amount for Remaining Prescription. | 10 | Eliminates this Requirement |
| HCP can Provide no Automatic Follow up and Enrollment into Compliance/ Savings Programs for Long Term Medications. | 11 | HCP can Enroll Patient into Available on-going Savings and Support right from SampleMD |
| Physical Samples are not Reported or Tracked by HCP or Health Group to Determine Outcomes | 12 | HCP and its Group can Track Sample and Co-pay Redemptions to Insure Patients Complied right from SampleMD. |
| Patient has no Option for Future Savings Program. | 13 | Patient has Option to also Enroll in Other Available Savings for Additional Prescriptions they take. |

SampleMD
alternative sampling support system

Enter a medication or condition below

Print FREE patient sample vouchers and co-pay savings

Enter Professional Information   *Required Field

*First Name:
*Last Name:
*Zip:
*Email:
*Confirm Email:
*Create Password:
Affiliation / Group#:
*Professional Designation:
*Speciality:

To verify your status as a licensed health care professional, please provide one or more of your license numbers:

State License Number (SLN)      State

Drug Enforce Agency Number (DEA)

Download

☑ Check here if you prefer not to provide a license number at this time. (Note that you will not be able to access select content and services in the future.)

Download & Registration
- This information is required to set up & access select content and services
- Download of your office SampleMD will occur immediately on this computer. You can also set up multiple computers by re-entering your Professional information on each laptop or desktop.
- We are committed to safeguarding your information. To learn more, please our Privacy Policy

FIG. 11

SampleMD
alternative sampling support system

Enter a medication or condition below

Print FREE patient sample vouchers and co-pay savings

Please fill-in following information one time

Last Name:

State License Number       DEA Number
                    OR

State

AL ▼        Submit

SampleMD
alternative sampling support system

Enter a medication or condition below

"Brand Name" or Condition

Print or eSend
FREE
patient sample vouchers and co-pay savings

30 Day Trial

Newly prescribed? "Brand Name"
Free 30 Day Trial Voucher

$15 Off Co-Pay

Already taking? "Brand Name" Savings Coupon up to $15 off patient co-pays

FIG. 12A

SampleMD
alternative sampling support system

Enter a medication or condition below

"Brand Name" or Condition

Print or eSend
FREE
patient sample vouchers and co-pay savings

30 Day Trial  ✕
Newly prescribed? "Brand Name" Free 30 Day Trial Voucher

For Formulary Status, Select Insurer Below.

Patient First Name*

Patient Email*   (Why?)

Gender*  |  Zip Code*  |  Doctor Last Name
Male ▼

Drug Formulary Status
Priority Health Plan ▼

Prescribing Information
"Brand Name" ▼

Search other brands of click
View | Print | eSend

Help Desk: (555)-555-5555

○ Pharmacy 1  123 Main St  (555) 555 - 5555
              Your Town, State

○ Pharmacy 2  123 South  (555) 555 - 5566
              Your Town, State

⦿ Pharmacy 3  123 North  (555) 555 - 5522
              Your Town, State

Search: | Cancel |          | State ▼ |

FIG. 14A

Dr. John Doe, MD
123 North St. Your Town, State 12345

(555) 555 - 5551    Confirm DEA #   AV3545165

Rx  Date  Patient First Name  Patient Last Name

Patient Address   City   Zip   State ▼

Drug Name  Dose   SNG   Qty: ▼   Refills ▼

Add Another Prescription

Notes:
Take with fish oil pills

View | Print | eSend

☑ I agree to Terms & Conditions
Please insert my electronic signature.

Help Desk: (555)-555-5555

FIG. 14B

SampleMD
alternative sampling support system

Print or eSend FREE patient sample vouchers and co-pay savings

Enter a medication or condition below

30 Day Trial ✕

Newly prescribed? Drug Free 30 Day Trial Voucher

Drug Company 1: Preferred Brand

Patient First Name*

Patient Email* (Why?)

Gender* — Male ▼

Zip Code*

Doctor Last Name — Doctor Smith

Drug Company 1 ▼

Prescribing Inform ▼

Samples From Rep ▼

Admin/Reports ▼

Search other brands of click

View | Print | eSend

Help Desk: (555)-555-5555

FIG. 19A

VIRTUAL SAMPLE CABINET SYSTEM AND METHOD FOR PRESCRIPTION DRUG MARKETING

CROSS-REFERENCE TO RELATED APPLICATIONS

This application claims the benefit of U.S. Provisional Application No. 61/273,960 filed on Aug. 11, 2009 and proceeding revision U.S. Provisional Application 61/277,161 filed on Sep. 21, 2009. The disclosure of the above applications are incorporated herein by reference.

FIELD

This disclosure relates to systems and methods for the business practice of marketing and distributing prescription drug sample vouchers and co-pay coupons by providing means to create, promote, print or electronically send, and track sample vouchers or discount offers, while assisting healthcare providers (HCPs) with a more convenient way to locate, determine and select—via their desktop computer, cell phone or other mobile devices—the most appropriate drugs and savings for their patients.

BACKGROUND

The statements in this section merely provide background information related to the present disclosure and may not constitute prior art.

Need for Improving Prescription Sample Distribution

The marketing of prescription drugs and the distribution of drug samples needs to be improved to meet multiple requirements of all the participants in the process. This group includes the drug manufacturers whose access to healthcare providers have been limited; physicians and other healthcare providers who must comply to greater regulations and processes; and also patients who need help in affording their rising out-of-pocket prescription costs. Because of time constraints in their practices, which translates into the need to complete more billable consults per day, up to 35% of physicians no longer will set aside time in their busy schedules to meet with drug sales representatives or accept physical drug samples.

If physicians do accept physical samples from drug representatives, they must then shoulder the time and efforts associated with meeting the increasing industry compliance factors required in recording their stored and distributed physical drug samples. This inventory logging responsibility is a major disincentive to doctors already burdened with record keeping and paperwork and feeling pressure to minimize their non-reimbursable activities. With prescription drugs currently accounting for around 10 percent of all health spending, physicians are always looking for a better ways to help patients get started and then maintain them on a prescribed branded drug. [www.nytimes.com/2009/01/06/us/06healthcare.html].

Additionally, physicians and other provider staff struggle to manually access the right information to determine patient's insurance reimbursement coverage for the selected medication they are about to prescribe. Therefore, with a growing number of physicians no longer seeing drug representatives, along with increasing compliance and "hassle" factors associated with selecting, managing and recording allocation of physical drug samples, doctors are looking for a better way to help patients get started and maintain on a prescribed branded drug.

Drug manufacturers are under increasing pressure to lower their prices for branded drugs all while their costs for bringing new drugs to the marketplace are continuing to rise without abatement. Research methods, which are continuously becoming more sophisticated and therefore expensive, are a large part of the costs to pharmaceutical manufacturers, which are to some extent unavoidable. However the second largest expense for pharmaceutical manufacturers after research and development (R&D) is their marketing costs for providing free samples to doctors and healthcare facilities. [www.phrma.org/files/Cost_of_Prescription_Drugs.pdf] This cost, which is more discretionary than R&D dollars, is therefore, for several reasons, potentially a preferred source for spending reduction by the pharmaceutical companies.

With the high cost of drugs to individuals in out-of-pocket expenses, and with many alternative drug choices, almost all patients are looking for better ways to afford and stay on the branded medicines they have been prescribed. However several studies have shown that free "physical" drug samples tend to go to the wealthy and insured rather than the most needy. [http://health.usnews.com/usnews/health/healthday/080102/most-free-drug-samples-go-to-wealthy-and-insured.htm]

Therefore, while business pressures are on physicians to reduce participation in "physical" drug sampling, and drug companies to decrease their spending on drug incentives, their patients are ever more needy of ways to insure they can both benefit via a free trial period, using particular drug samples, and economically maintain, via co-pay savings, on their drug therapy.

Prior Art in Drug Sample Management

Despite technological advances afforded by prescription management systems, computer programs for presenting information related to pharmaceuticals, ability to order physical samples online and computerized systems for tracking drug samples, several critical weaknesses remain in optimizing the distribution of prescription samples using healthcare providers. One prior solution employs scanning and optical recognition to assist in scanning information into the system which can then be checked with rules-based processing for conformation with protocols before routing to the dispensing pharmacy (U.S. Pat. No. 7,493,263) Another prior solution creates a computer based system which employs inventory management and bar code scanning to track samples between sales representatives and health care practitioners. (U.S. Pat. No. 6,952,681) Barcodes are utilized in an alternate fashion by another system by which a physician enters prescription information into their computer which then prints out a bar coded prescription. The printout of the prescription is taken by the patient to the pharmacy where the pharmacist then uses a bar code scanner to automatically enter the prescription information into the pharmacy computer. (U.S. Pat. No. 5,883,370)

Yet another prior invention uses a secure network and communications to send approving instructions to a remote dispensation station. (U.S. Pat. No. 6,735,497) A patient can be given a free drug sample simultaneous with generation of the actual prescription and a peel-off label to be affixed to the patient's chart by use of a pharmaceutical marketing device previously disclosed. (U.S. Pat. No. 5,803,498) Another prescription creation systems automatically divides the prescription into two parts. The first is fulfilled quickly and locally and the second associated prescription enjoys cost savings by virtue of being fulfilled by remote mail order. (U.S. Pat. No. 5,737,539)

A multi-part form has also been used to facilitate the collection of demographic information from pharmacists on the special multipart vouchers filled by physicians with patient demographic information. (U.S. Pat. No. 5,628,530) A medical center computer, central server, and computers from multiple drug companies comprise a network to enter and store information regarding the receipt, dispensing, and inventory of drug samples. (US Pat App. 2003/0216974) A local medical information management system is used to prescribe a particular product, and with acquisition of a specific sample, the machine reading capability of the system is used to acquire the sample information and associate it with the medical record for the particular patient. A full prescription can also be more easily issued at this point. (US Pat App. 2002/0013787) A similar prescription writing system which also tracks sample distribution but in a special sample distribution database which can be analyzed by a number of parties including drug manufacturers, pharmacies, and advertisers. (US Pat App. 2003/0212577)

As listed, a number of proposed systems improve the prescription writing process or assist in the management and distribution of drug samples. But, in actuality, there is no current system, which integrates the full abilities for all parties involved to most efficiently participate in both the prescription drug sample distribution and drug promotion processes. As a result, drug samples are decreasing in popularity and patients are not able to enjoy their intended benefits most of the time. Additionally, drug representatives operate at a fraction of their potential due to increasingly limited access from those willing to see them.

Prior Art in Drug Sample Based Consumer Marketing

Probably the most prevalent means to attract customers to a particular drug has been through specific direct-to-consumer sales advertising in multiple media channels. However the ubiquity of this style of mass promotion has also become one of its weaknesses. This is because of the massive amount of disparate adverts, which come in the mail, through newspapers, television commercials, and via web advertising. The volume from these marketing channels has become so large as to overwhelm the public consumers and provide on-going concern from the government and its threatened legislation against direct-to-consumer advertising by the drug industry.

In addition, in order to take advantage of drug discount offers requires a self-education process by the patients to determine drug alternatives for their particular conditions. After a self-education phase, patients must perform a research phase to look for relevant discounts, and then either personally analyze these results or compile them all for future discussion with an HCP that has final prescribing ability. There are clearly so many steps to a patient obtaining a prescription in this manner, that only a small minority can realize savings on their prescriptions in this way. These factors have led prior inventors to try to surmount these problems for example by improving the actual physical distribution of drug samples, by facilitating the tracking of physical samples, or by recording coupon redemptions for database analysis.

Some conventional prescription management systems have a large number of options for capturing patient information. Other systems provide the ability to order physical samples and vouchers online and track sample handling and even create databases regarding sample distributions for analysis by drug manufacturers. Yet, there are no existing systems that provide the means to minimize the burden of sample inventory control, centrally access product and patient insurance reimbursement information and record if and how samples were used and allocated by HCPs, while at the same time as providing the most convenient means for patients to obtain cost savings directly through their doctors office. To date, no sample inventory control systems or prescription management systems have been able to significantly minimize the overall efforts required from the parties involved in the existing drug sampling processes.

FIG. 2 illustrates a functional overview of the participant interactions and management operations that currently are typically practiced during the distribution of physical prescription drug samples utilizing conventional methods that are presently available. The arrows in FIG. 2 show flow of communications between the participating parties. The disbursers, of the drug samples, are healthcare providers 4 which may include among others physicians (MD), nurse practitioners, and doctors of osteopathic medicine (DO). The other parties participating in the prior art distribution of drug samples are drug company manufacturers 6 and salespersons 3, pharmacies 8, and patients 2. As shown, a real location for storage of the physical drug samples or an Rx sample cabinet 101 is also integral to prior art processes.

FIG. 2 enumerates the main drug sample management functions 210 as practiced in prior art. Each of the eleven sample management functions 210 requires at least two member processes to complete the function. These are a patient or drug rep process 230, a healthcare provider process 240, a physical sample cabinet process 250, or a pharmacy or drug manufacturer process 260.

FIG. 2 shows the first physical sample distribution function 210 is Drug Manufacturer makes samples and packaging and ships supplies to Drug Representative 211. Drug manufacturers must create additional drug samples for their giveaways and promotional trials. They must also design and manufacture special packaging. This dedicated packaging for small sample sizes must also be created to be attractive, safe, protective and also conducive for display and transportation purposes. These packaging and associated drug sample costs have become a significant fraction of the overall marketing budget for drug manufacturers 6. Yet these extra costs are presently unavoidable with the distribution and inventory of drug samples being currently held in the offices of health care providers.

As shown in FIG. 2 after the drug manufacturer creates the drug samples or vouchers and packages them in sample packaging, the drug samples 10 are shipped to the drug representatives 3 for their distribution to health care providers 4.

FIG. 2 shows the second physical sample distribution function 210 is Drug Rep supplies HCP with Rx drug samples and discount vouchers for Rx Sample Cabinet 212. The drug rep 3 meets with the healthcare provider 4 to provide the drug samples. The HCP is required to login samples 213 in order to meet industry compliance standards, such as the Joint Commission on the Accreditation of Health Care Organizations (JCAHO), as they are placed into the inventory in the Rx sample cabinet 101. The HCP treats patient 214 and uses medical expertise and knowledge of the patient 2 to determine the medical diagnosis, which needs to be treated. Once this determination is made, HCP searches inventory of Rx sample cabinet for appropriate branded sample or voucher 215. Then HCP manually reviews insurance coverage of sample 216 by looking up the patient's formulary reimbursement status for the selected product to make sure it is covered by their insurance provider. Then HCP logs out sample 217. The login 16 and logout 18 into or out from the Rx sample cabinet 101 are dictated by regulatory compliance requirements of the pharmaceutical industry among other requirements.

Next the HCP 4 performs the dual function of Rx physical samples & coupons selected; HCP writes Rx prescription for Patient 218. The HCP 4 provides the patient 2 with physical drug samples 10, or a paper coupon 12, which is a form of proxy for the drug sample 10 which can be redeemed for discount value at the pharmacy of choice for patient 2. Trial versions or physical drug samples 10 are not intended to provide a full course of drug treatment, therefore in most cases the HCP 4 will find it necessary to complete the drug regimen, and will write a drug prescription 14 for the patient 2 to complete the balance of the quantity necessary.

Patient starts sample then takes prescription and coupon offers to pharmacy to fill balance of Rx 219. In some variations the HCP 4 has the ability to directly send the drug prescription 14 directly to the pharmacy 8 by electronic means. Next Patient checks level of Rx and refill allowance; contacts Pharmacy or HCP when refills are needed 220. As shown in FIG. 2, currently when a patient 2 runs out of drugs the burden is upon themselves to notify their prescribing HCP 4 in order to renew the prescription 14. In most cases the free drugs or sample trial is over. Therefore, Patient is required to pay full amount for remaining prescription, once sample or trial voucher runs out 221.

As shown in FIG. 2, the management process in prior art is extremely expensive in time, effort, and expense for the drug manufacturer 6 to (1) manufacture the sample drugs or discount vouchers 10 to be supplied for their drug representatives 3, (2) pay the salaries and expenses of the drug reps 3 and their to visits to educate HDP's 4 and stock their drug sample cabinets 101, and (3) to design and develop special packaging optimized for the small sample dosage sizes.

Prior art drug sample management and distribution is also onerous on the HCP 4 to meet with drug reps 3, and conform to compliance regulations. The patient 2 must also juggle multiple drug sources and payment options while shouldering responsibility for tracking their prescription coverage timing.

Therefore, all of the above mentioned systems are still deficient in their ability to serve as a complete platform, which allows drug manufacturers to develop, promote, and manage drug samples and savings offers, and to aid in their disbursement by HCPs to patients.

SUMMARY

The present disclosure introduces a new method to assist with distribution of prescription drug samples and provide co-pay vouchers to thereby increase patient affordability and compliance to their prescribed drug regimens, mitigate risks and safety factors in drug handling and prescription verification, and increases productivity of HCPs and profitability to drug manufacturers. These advantages are achieved by a computer program run either by remote access on a central server system or by simple download of the client application software direct to a desktop computer, cell phone, or other mobile devices. Alternatively the method can be run by access through an Electronic Medical Records system to search, print or electronically dispense drug samples and co-pay coupons through a national network of pharmacies. Use of the disclosed system eliminates the need for primary health care facilities to manage and store physical drug samples by offering them a more convenient and efficient way for HCPs to select, allocate, administer and report distribution of needed samples and co-pay savings to their patients.

The novel system, which provides this method for drug sampling and patient savings support, is the Virtual Sample Cabinet (VSC) system. For brevity and development purposes the present invention is termed "SampleMD". (www.samplemd.com) The VSC method and system reduces the bookkeeping burdens over conventional ways currently being used to select, distribute and track physical drug samples. This "virtual prescription drug sample cabinet" assists doctors and staff in determining the right sample medication, to print or electronically send sample vouchers and co-pay coupons right to pharmacies directly from their desktop computers or mobile devices, and automatically records the transaction details. Healthcare providers are also assisted beforehand in determining the sample right medication to select based on instant access to product and prescribing information as well as the branded drug's "formulary status" within the patients' insurance plan to determine what level the prescribed product will be reimbursed for each searched brand drug.

In other features, the VSC system and method also provides available on-going savings and educational support for registered patients through automated email communications and delivery of monthly or periodic co-pay refill savings offers. These reminders then serve to promote continued drug compliance for patients with chronic conditions such as diabetes, heart disease and asthma.

Following secure login, users of the VSC system, including physician's offices, affiliate groups of health care providers, insurers, and product manufacturers, can track and generate various reports which summarize various analyses of patient use and redemptions of discount vouchers, as well as the effectiveness of the drug promotions within a national network of participating pharmacies.

The VSC system consists of: (1) system database access and security interface subsystem, (2) formulary maintenance assistant, (3) offer creation and maintenance assistant, (4) sample dispensing assistant, (5) automated patient follow-up assistant, (6) promotion reporting assistant, and (7) virtual sample cabinet data center. In other features, an update of the internal databases, within the virtual sample cabinet data center, can be performed by synchronization to the remote central system server through an Internet connection. The VSC system can alternatively either include or interface with a printing device that makes a hardcopy duplicate of the selected coupon for provision to redeeming pharmacies, as well as an auto e-fax and other electronic transfer components to send directly to the selected pharmacy.

BRIEF DESCRIPTION OF THE DRAWINGS

FIG. 8 is a side-by-side summary of the management processes for creation, distribution, and follow-up of prescription drug promotions as practiced by prior art as compared with the virtual sample cabinet according to various aspects of the present disclosure.

FIG. 10 shows a representative screen layout for entry of information for the creator of a new health care provider account as part of the download and registration setup of the desktop software for the virtual sample cabinet system, in accordance with a SampleMD embodiment of the present invention.

FIG. 11 shows a representative screen layout for entry of information for the new health care provider as part of the setup of the desktop software for the virtual sample cabinet system in accordance with a SampleMD embodiment of the present invention.

FIGS. 12a and 12b shows representative screen layouts for doctors or staff to search samples and savings information using the virtual sample cabinet system in accordance with a SampleMD embodiment of the present invention.

FIGS. 13a and 13b shows representative screen layouts for doctors or staff to search formulary status and lookup insurance coverage for a product using the virtual sample cabinet system in accordance with a SampleMD embodiment of the present invention.

FIGS. 14a and 14b show representative screen layouts for entry of information for the health care provider to send to a selected pharmacy the generated prescription or print out for patient as part of the virtual sample cabinet system in accordance with a SampleMD embodiment of the present invention.

FIGS. 19a and 19b shows several representative screen layouts for creation of drug prescribing information by the drug manufacturer companies as part of the database creations utilized by the virtual sample cabinet system in accordance with a SampleMD embodiment of the present invention.

DETAILED DESCRIPTION

Figure 1:
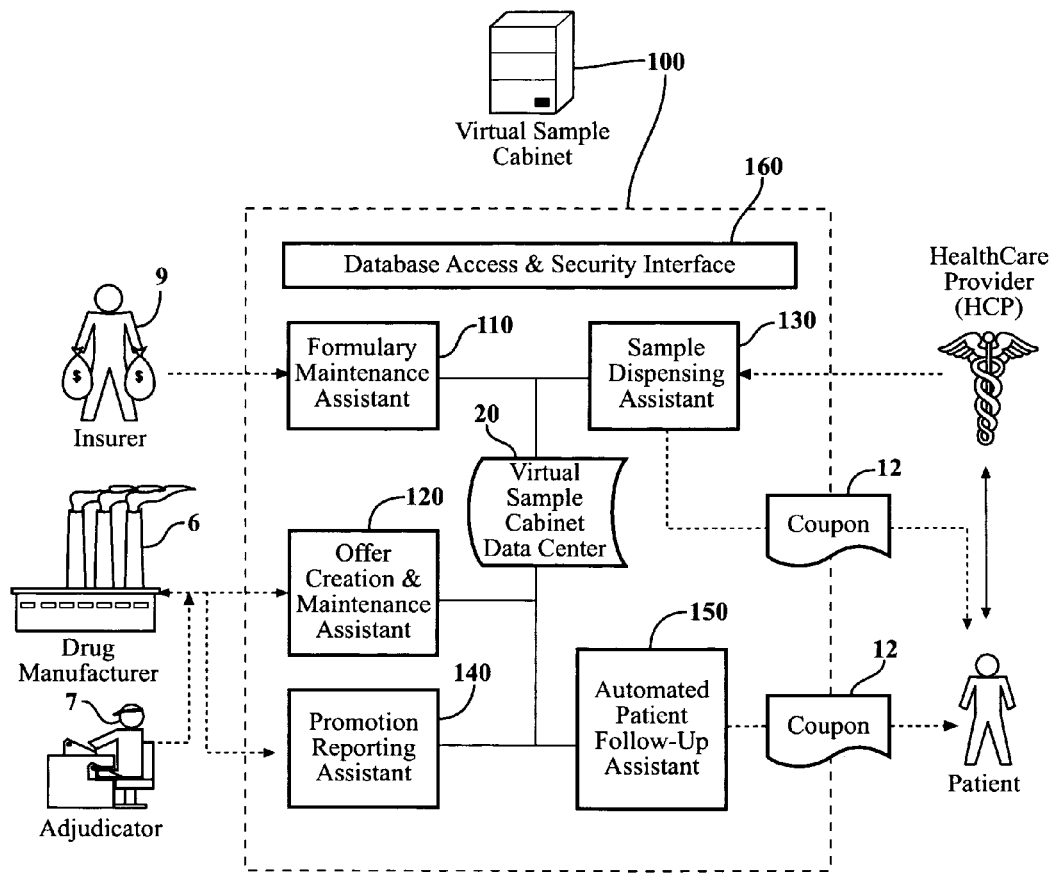
FIG. 1 shows a high level overview of software subsystems comprising a computer system that performs the methods of a virtual sample cabinet for prescription drugs

The following description is merely exemplary in nature and is not intended to limit the present disclosure, application, or uses. It should be understood that throughout the drawings, corresponding reference numerals indicate like or corresponding parts and features.

The following discussion assumes the reader is familiar with health care standards for the writing of drug prescriptions, prescription drug promotional processes, medical insurance for prescription drug coverage, and requirements for medical software and patient record communications.

The present disclosure describes various embodiments of methods for using a "virtual sample cabinet" (VSC) that allows doctors and staff to print or electronically send sample vouchers and co-pay coupons right to pharmacies—directly from their desktops.

In exemplary embodiments, doctors and health providers will download a software application right to their desktops from a dedicated website or access it through their Electronic Medical Records system to search, print or electronically dispense drug samples and co-pay coupons through a national network of pharmacies. This minimizes the need for physician offices to manage and store physical drug samples because the novel VSC system offers a more convenient and efficient way to allocate, administer and report needed samples and co-pay savings to their patients.

Various embodiments provide for the VSC system that through its unique software and system interfaces allows doctors to review a branded drug's "formulary status" within the patients' insurance plan to determine what level the product is reimbursed, look up prescribing information and other product information from the searched brand drug. Unlike promotional processes based strictly on provision of physical samples, the disclosure herein also provides on-going patient support through automation of email communications and delivery of monthly co-pay refill savings to thereby promote continued drug compliance for chronic conditions such as diabetes, heart disease and asthma.

In preferred embodiments, each voucher or discount coupon redemption can be tracked and reports generated by physician offices, affiliate groups, product manufacturers and other parties as the new methodology provides for logging and integration within a national network of reporting pharmacies.

Without the deficiencies of prior art, the present invention can be advantageous to drug manufacturers who are making pharmaceutical products which they need to promote, health care providers who need to minimize drug costs for filling their prescriptions, insurers who are desirous to improve communication of their reimbursement policies, pharmacies that prefer to maintain oversight of all drugs consumed by patients, and the patients themselves in order to realize the maximum savings on their medications while minimizing their effort to achieve this goal.

The organizations listed are highly motivated to achieve return on their financial or other type of investment in drug promotions. Their spending on marketing therefore needs to be evaluated in terms of its impact on the patient customer base. The impact thus measured will then allow quantitative measurement of the performance of each incentive program and make it possible, based on this information, to maximize logistical and economic efficiencies of the overall marketing campaign. This measurement process is automated with reporting capabilities of the disclosure.

Various embodiments provide for a novel virtual sample management system that, through its new and unique combination of software and system interfaces, significantly increases the ability of a drug manufacturer to design and implement the discount incentive promotions for its prescription drugs. At the same time, healthcare providers can search and locate the optimum drugs for their, patients that will not only be compatible with their insurance coverage, but also minimize their out of pocket expenses because of the discounts located from existing incentives. The various parties that utilize the virtual sample management system all benefit from monitoring the effectiveness of the system in helping them perform their respective roles in the distribution of prescription drug savings.

For example, by using the VSC system, patients can better track their own compliance with their prescribed regimen. They can also track their total savings to date. HCPs can likewise evaluate how much they are saving their individual patients. But HCPs can also use the VSC system to determine the savings they have helped any groups of their patients to realize. At a higher level, the affiliated provider groups, which each supervise a group of health care providers, can for example, using the VSC system, compare the savings provided to patients by their constituent physicians and make use of this analysis to make suggestions as to what prescription regimens are most effective within their provider groups.

In the context of this disclosure, adjudicators provide a mechanism for a pharmacy to request approval from a health plan to authorize certain prescription drugs, as required by the patient's health plan contract. In this role, adjudicators benefit from the VSC system as they can quickly run reports similar to those above and give summary reports to their client insurers and drug manufacturers and thereby more easily demonstrate the volume of drug incentives they are promulgating.

These system capabilities enable the more widespread use and encourage frequent employ of VSC by healthcare providers, and drug manufacturers of the present invention and therefore there is created a positive feedback cycle. That is, the VSC method and system increase the speed for evaluating the drug alternatives and most advantageous savings available to a particular patient. The decreased time needed for these evaluations results in improved accuracy of the evaluation. HCPs then have more time available to spend with their patients since they no longer have the need to login and logout physical samples, check through drug formularies, and search for drug discounts among other activities.

Similarly the savings realized by drug manufacturers in not having to create the physical drug samples along with their packaging and expenses associated with drug representatives distributing these samples will allow them to give larger, more frequent promotional discounts or incentives to attract and retain suitable patients and form a positive feedback cycle.

The discount coupons are either sent directly to the patient selected pharmacy by the HCP using the communication capabilities of the VSC system, or carried by the patient to the pharmacy as a coupon or co-pay discount generated by printout from the VSC system. The VSC system and method therefore leverages the centralized medication database of the pharmacies to perform a comprehensive and secondary check on the potential risk of negative drug interactions. Patients are more likely to fulfill their prescriptions at a single convenient or favorite pharmacy location or even at a branch of belonging to their favored chain of pharmacies than they are to rely upon a single HCP for all their healthcare requirements.

To a large extent drug manufacturers are not currently able to evaluate the effectiveness of their drug samples or voucher discounts. This is because in actuality good records are not kept by HCPs of the exact patients that received samples and moreover, there is not any association or follow-up after a sample trial to judge whether the trial results in an actual short-term or long-term prescription being made. This current situation is greatly improved upon with the accuracy of analysis using the VSC method and system. This decreased cost and increased accuracy in analysis of promotion effectiveness will in turn result in widespread use of the system and methods by manufacturers and HCPs, which itself in turn then engenders enhanced customer participation and response. Therefore the VSC system engenders a cycle of increased speed to create promotion, decreased packaging costs, decreased physical samples and drug reps costs, increased accuracy of evaluation, and increased marketing effectiveness.

As can be appreciated, the method and system for the virtual sample cabinet are applicable to various members of pharmaceutical related industries, including, but not limited to, drug manufacturers, healthcare providers, medical insurance companies, and adjudicators, pharmacies, and patients. Essentially all kinds of drug manufacturers can make use of the invention to promote their particular products. Although the methods and systems are applicable to various communication channels and healthcare providers can access the invention on various hardware apparatuses including cell phones, wireless portable digital assistant devices, laptop computers, and even through dedicated kiosks, for ease of the discussion, the remainder of the disclosure is presented in the context of desktop computer systems.

An exemplary system implementing the new methodology is called Virtual Sample Cabinet and at the most general level may include: (1) system database access and security interface subsystem, (2) formulary maintenance assistant, (3) offer creation and maintenance assistant, (4) sample dispensing assistant, (5) automated patient follow-up assistant, (6) promotion reporting assistant, and (7) virtual sample cabinet data center. It is appreciated that the modules and data structures shown may be combined and/or further partitioned to similarly perform enhanced drug sample and discount voucher promotion and distribution. Various embodiments of campaign management and optimization methods and systems include alternative implementations and combinations of the above described elements as will be described in more detail below.

For the sake of simplicity of description, an exemplary diagram of the VSC system is shown in FIG. 1. The solid connectors in FIG. 1 show the flow of communications between various VSC system subsystems. The dashed arrows from the various participating parties to the VSC system 100 signify secure system communications mediated through the database access and security interface subsystem 160. A formulary maintenance assistant subsystem 110 serves for direct entry or import of drug compensation configuration, from medical insurers 9. The offer maintenance assistant subsystem 120 is used by drug manufacturers and/or insurance adjudicators to create the details of a promotional offer for a prescription drug.

The sample dispensing assistant subsystem 130 is used by healthcare providers 4 to assist in locating the appropriate and optimum drug discount offers in the form of a coupon 12 to proffer to their patient 2. Not shown in the figure is that the coupon or discount offer can also be sent directly to the pharmacy 8 preferred by the patient 2.

The promotion reporting assistant subsystem 140 allows parties with access rights through the database access and security interface 160 including drug manufacturers 6 and/or insurance adjudicators 7 to generate standard or custom reports which summarize or compare the effectiveness of their various drug discount campaigns.

The automated patient follow-up assistant subsystem 150 uses information stored in the virtual sample cabinet data center 20 to monitor the timing, dosages and number of pills in the offers received by all patients 2 in the database. When the analysis performed by the follow-up assistant subsystem 150 predicts that a patient is close to running out of medication and that the medical condition of the patient 2 has a likelihood of requiring a prescription refill this subsystem can send a continuation discount coupon 12 along with personalized reminder and tailored medical counseling information directly to the patient 2. In this fashion patient compliance is encouraged and incentivized in a timely fashion.

These subsystems operate and interact with the central registry of information contained within a virtual sample cabinet data center 20. The VSC data center 20 comprises a formulary status database 22, VSC user accounts database 23, sample vouchers and co-pay coupons or offers database 24, disease and prescription drug information and promotion database 25, historical prescribed offers database 26, and fulfilled claim vouchers database 27, among other databases. The virtual sample cabinet data center 20 includes these various specialized databases which are necessary to permit the security operations to restrict access to sensitive data but also to contain the specifics of the discount offers as well as the various insurance details necessary for the proper counseling to be made to best support selection of the discount offers and coupons 12 for each patient 2.

The present disclosure describes various embodiments of a virtual sample cabinet system and method that comprise means for management of drug vouchers and coupons distribution. The drug discount incentives include among others: (1) coupons, (2) co-pay vouchers, (3) discounts, (4) updates, (5) background medical conditions and (6) supplemental drug information.

The system of the present disclosure makes it convenient for the drug manufacturer 6 to offer any of these incentives to the HCPs in order to increase the likelihood of their offering these discounts in turn to their patients 2. The present disclosure makes it possible for drug manufacturers 6 to measure redemptions in off-line settings for their discount offers by database access to the centralized collection of the data required to perform this analysis. By collecting information from HCPs suggestions to patients, redemptions at pharmacies, and transactions processed by adjudicators, among other entries in the VSC data center, the effectiveness of offers from manufacturers in yielding redemptions can be assessed. In follow-up effectiveness, the VSC system 100 will either email an offer to a patient 2 or encourage a patient 2 to go to a website to printout a follow-up offer or coupon.

As shown in FIG. 1, the VSC system 100 contains all the interfaces, modules, databases, and data analysis tools to configure a prescription drug discount offer, provision follow-up offers and associated information, collect HCP and patient responses to the discounts, analyze these responses and use the response information in performing analyses which assist in the optimization of the drug discount marketing effectiveness.

Figure 2:
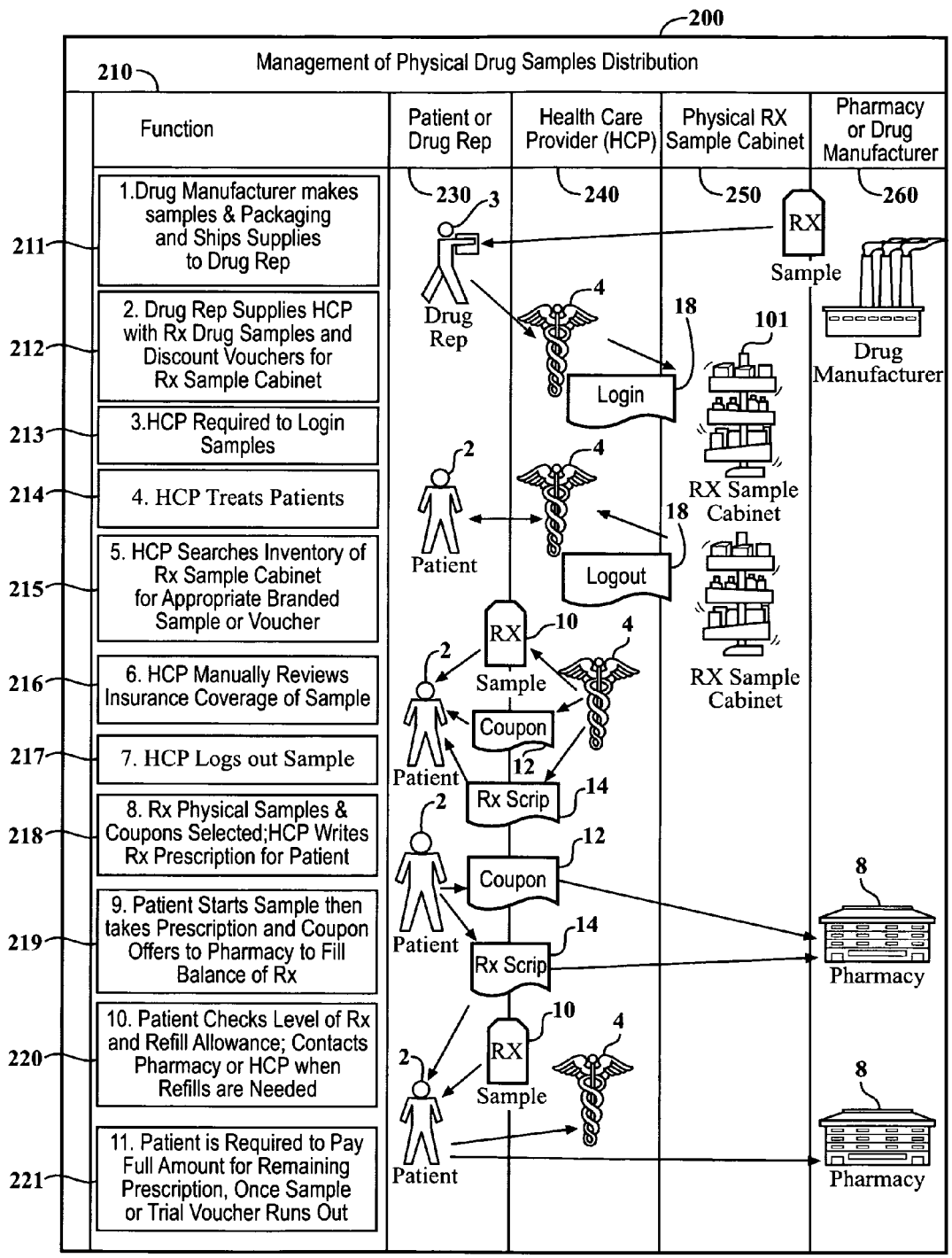
FIG. 2 shows a general overview of management of distribution of physical drug samples as practiced by prior art for pharmaceutical promotion processes.
Figure 3:
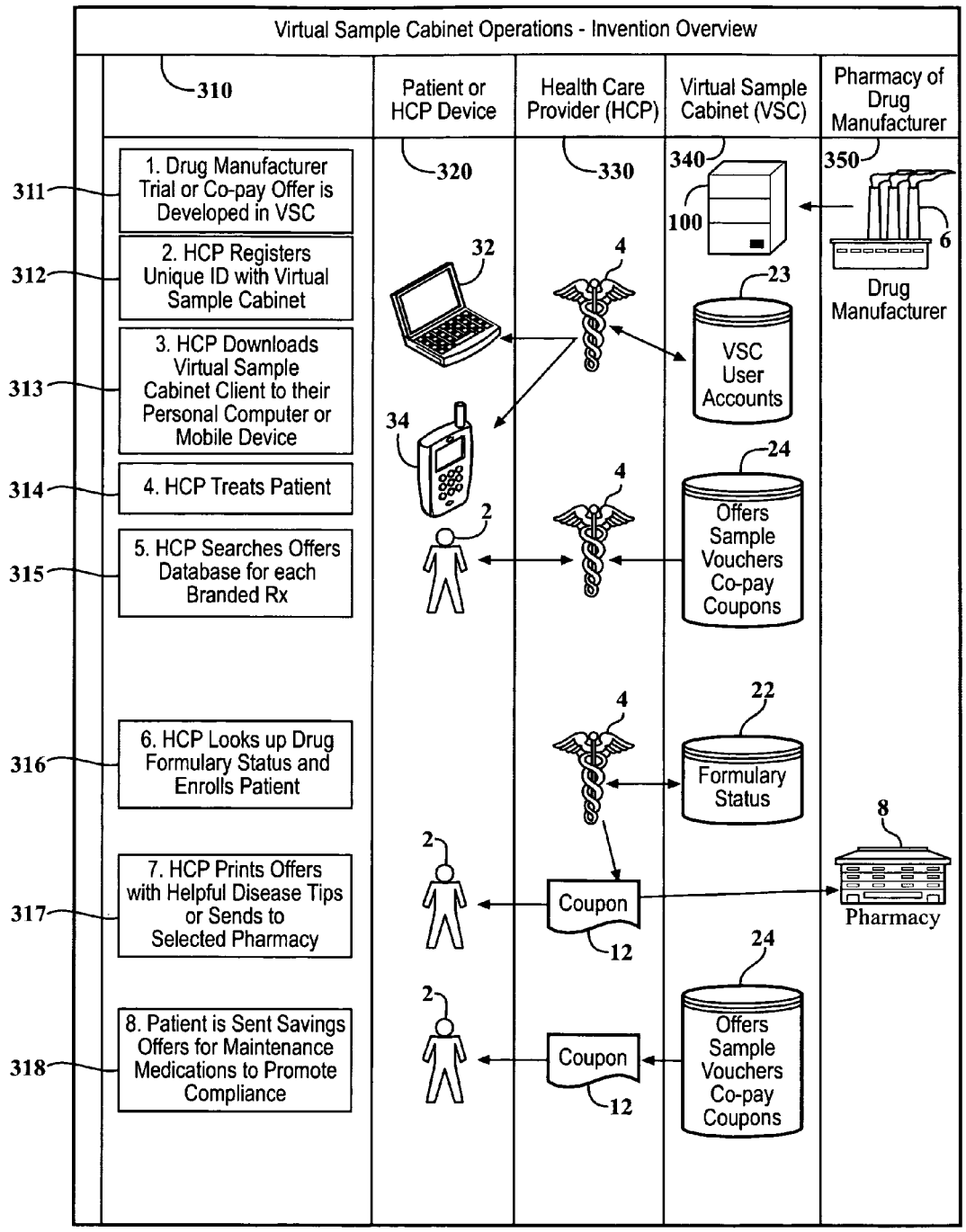
FIG. 3 is a system diagram illustrating operation of a virtual sample cabinet as an alternative to traditional marketing, management and distribution of physical samples according to various aspects of the present disclosure.

FIG. 3 is a high-level functional overview of the participant interactions and management operations of the virtual sample cabinet system and method for the distribution and tracking of drug samples and saving coupons for prescriptions utilizing an exemplary embodiment of the disclosure. The flowchart in FIG. 3 show the improvements upon the prior methods of prescription drug sample distribution management made possible by using the exemplary VSC system 100 as shown in FIG. 1. As can be seen in FIG. 3, the improved process for drug sample management and distribution employs a virtual sample cabinet 100, as contrasted with the prior art methods shown in FIG. 2, which employs a physical structure in an actual location for storage of physical drug samples or the Rx sample cabinet 101.

FIG. 3 enumerates the main drug sample management functions 310 in the present disclosure. Each of the eight virtual sample management functions 310 requires at least two member processes to complete the function. These are a patient or health care provider device process 320, a healthcare provider process 330, a virtual sample cabinet process 340, or a pharmacy or drug manufacturer process 350.

FIG. 3 shows the first virtual sample distribution function 310 allows the Drug Manufacturer to automatically create a trial or co-pay offer by simply entering the discount offer information into virtual sample cabinet 311. In this embodiment the drug manufacturer 6 merely implements an offer or discount program using the method and system of the invention and the discount offer details are stored within the VSC data center 20. The drug manufacturer no longer is required to create physical drug samples or individually printed discount vouchers, their packaging, and distribute these through the drug representatives 3.

FIG. 3 shows the second virtual sample distribution function 310 is HCP registers unique ID with virtual sample cabinet 312. This account is established in the VSC user accounts database 23 within the VSC data center 20. The HCP 4 uses the registration functions of the virtual sample cabinet 100 to establish a personal account. The HCP downloads virtual sample cabinet client to their personal computer or mobile device 313. As shown, alternatively to running the software on their desktop computer, the HCP can run a remote client on their laptop computer 32 or even smart phone 34. Similarly to prior art, at this stage, the HCP treats patient 314 and uses medical expertise and knowledge of the patient 2 to determine the medical diagnosis, which needs to be treated. However once this determination is made, HCP searches offers database for each branded Rx 315. The VSC system 100 handles all compliance reporting automatically and the HCP is not required to perform paperwork to login or log out physical samples.

Once HCP uses review capabilities of the VSC system 100 to search offers in the sample vouchers and co-pay coupons database 24 the HCP looks up drug formulary status and enrolls patient 316. Next, HCP prints offers with helpful disease tips or sends to selected pharmacy 317. The HCP 4 provides the patient 2 with a paper coupon 12 printout generated by the VSC system 100, or the system can directly communicate the discount coupon 12 to the pharmacy of choice for patient 2. In preferred embodiments, the HCP will provide prescription for the patient which includes a full course of treatment rather than an incomplete course of treatment which is frequently encountered when a physical sample trial is used to initiate a treatment as in prior art discount offers.

The VSC system 100 keeps track of all patients 2 that are treated using the system. The system can thereby automatically determine when the patient 2 can be encouraged to remain in compliant with the regimen initiated by their HCP 4. Therefore the next function is Patient is sent savings offers for maintenance medications to promote compliance 318. As opposed to requirements caused by prior art, the patient is not forced to assume the burden of seeking out additional discounts but the VSC system 100 assumes that responsibility.

This introduction of VSC system 100 in the present disclosure, results in the substitution in FIG. 2 of the physical sample cabinet process 240 for virtual sample cabinet process 340 in FIG. 3. This changed column and incorporated series of processes within are those that are conducted in a semi- or even fully-automated fashion by the exemplary VSC system.

The key processes, which are deficient in prior art, especially those requiring overly burdensome record keeping by HCPs, ineffective, incomplete searching for available offers, and inaccurate capture of patient compliance data are all formally and efficiently solved using the method of the present disclosure. Most importantly, the capture of the patient participation data is so accurate and immediate that the marketing efficiency can be analyzed in near real-time together with information about the regarding the past history and demographics of the treated patients. This timely analysis allows the VSC system 100 to create reports, which can improve prescription drug marketing performance.

Because the VSC data center 20 contains updated patient data the promotion reporting assistant subsystem 140 can be utilized by the drug manufacturer 6, adjudicator 7, HCP 4, or any authorized system operator to perform appropriate queries on the promotion data and other accumulated data in the VSC data center 20. Then this data is used to execute analytics which can be in turn used to generate graphics assessing the performance of the various promotions or to make automatic determinations of the discount performances and even make recommendations as to how to improve patient or HCP response based on location, scheduling, and associated advertising campaigns among others. The VSC system 100 can then even calculate the overall cost of the marketing promotion and the system operator on behalf of the drug manufacturer 6 can make the expedient changes in the drug marketing and promotions.

Figure 4:
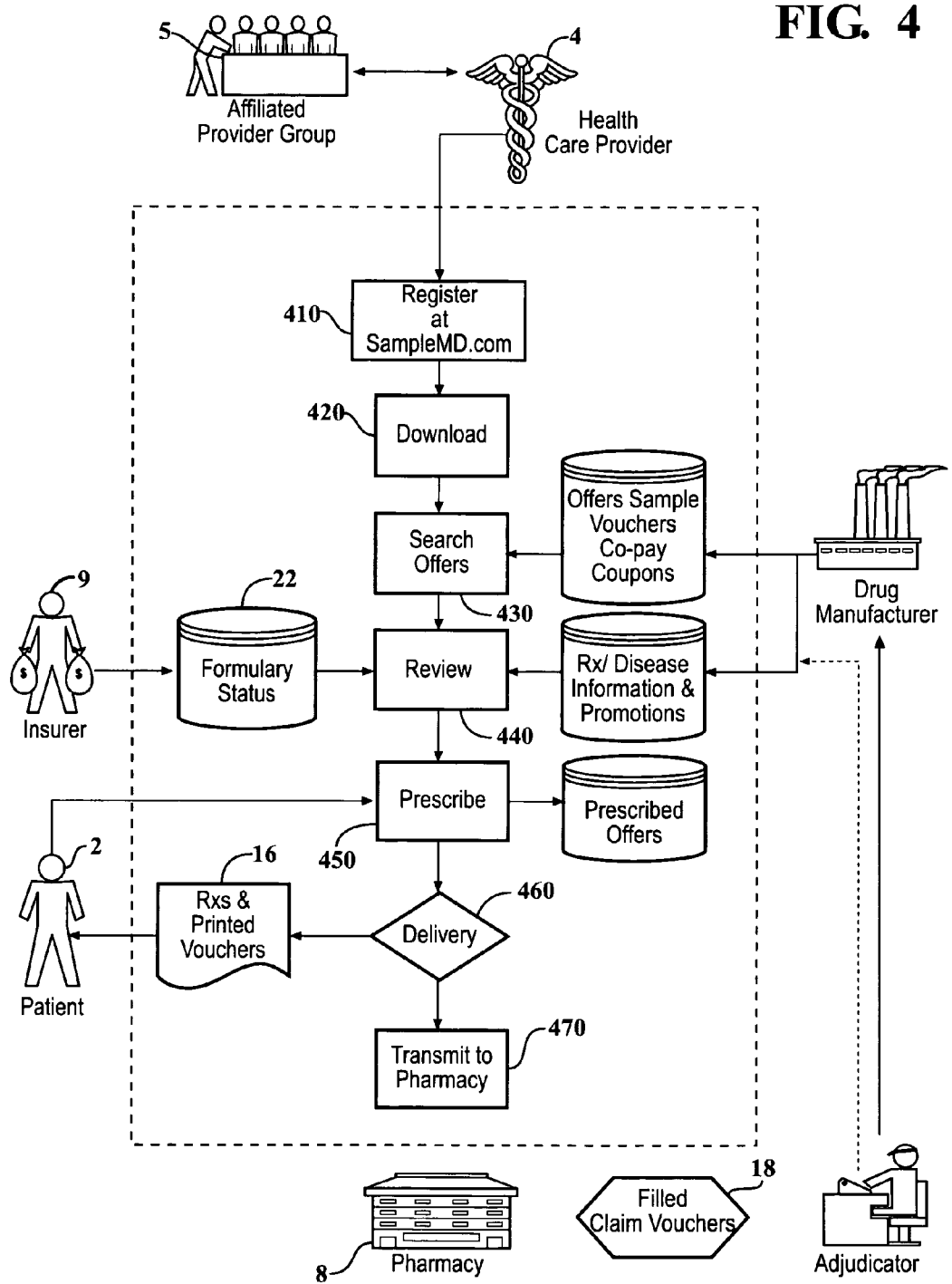
FIG. 4 is a high level diagram illustrating an exemplary process flow for usage of the system to enhance distribution and tracking of prescription drug samples and savings coupons for prescriptions within a health care environment according to various aspects of the present disclosure.

FIG. 1 shows the complete functionality and flow of the VSC system 100 for all aspects of drug sample management. However, FIG. 4 is a process flow diagram illustrating a method for distribution and tracking of co-pays coupons and sample vouchers for prescription drugs as performed within the virtual sample cabinet system 100. In particular, FIG. 4 is a process flow diagram strictly for illustrating a method of registration and distribution of the offers as performed primarily using the software modules within the sample dispensing assistant subsystem 130 of the overall VSC system 100. The arrows in FIG. 4 show the flow of communications between the main system modules.

The register process 410 allows the healthcare provider 4 to enter their individual information, which is necessary for them to be permitted access to functionality to write prescriptions and track drug dispensing data. This will involve some form of secure identification that can be used for future login verification. Once a user is registered within the system, in the future, they can login and upon authentication of their identity through an authentication process can perform the processes for which they have permission. The download process 420 serves for allowing the healthcare provider 4 to connect to the dedicated Internet domain (ex. www.SampleMD.com) and download to their own desktop computer the software application, which performs the methodology disclosed herein, for drug sample distribution and tracking. Once the caregiver is registered, they are ready to perform the search offer process 430, to find discounts on prescription drugs appropriate for the patient 2 they are currently treating.

As shown in FIG. 4 the drug manufacturer 6 creates in advance the offers database 24 which contains all the sample vouchers and co-pay coupons that they would like to use to incentivize patients 2 to try their drug. The drug manufacturer 6 also creates the disease and Rx information and promotions database 25 which includes the supplemental marketing literature that the HCP 4 and patient 2 can use together or individually to inform their drug treatment decision making.

The review process 440 is the next step in the flow of operations. The HCP has identified a single or group of appropriate drugs. The providers of medical coverage or insurers 9 based on their economic analysis and medical understanding they create the list of preferred and covered drugs for the spectrum of medical conditions and thereby contribute their entries into the formulary status database 22. By review with the formulary status database 22 and the other additional drug information, the HCP identifies the drugs with discounts that could meet the needs for treatment of the patient 2.

The HCP 4 performs the prescribe process 450 in consultation with the patient to select the preferred drug(s). The caregiver then verifies the formulary status of the selected drugs and prescribe process 450 to create a virtual medicine shopping cart for the patient 2 which are entered into the prescribed offers database 26. The delivery process 460 facilitates the mode of delivery of the savings to the patient 2. Based on preference of the patient 2, the HCP 4 can print out a paper version of the discount voucher and associated prescription 16 for the patient to take with them. Alternatively, the HCP 4 performs a transmit to pharmacy process 470 of the drug prescription and electronic discount voucher or coupon to a pharmacy 8 selected by the patient 2. The patient 2 then visits the pharmacy 8 of choice with their coupon or just presents their identification to fulfill their discounted prescription.

The pharmacy fulfills the drug sample voucher or discount offer by entering the associated patient ID, bin number and other required claim information to bill the respective product manufacturer or vendor. From there, the redemption verification of the generated offer is reported back to the VSC central server system 100 for reporting.

Figure 5:
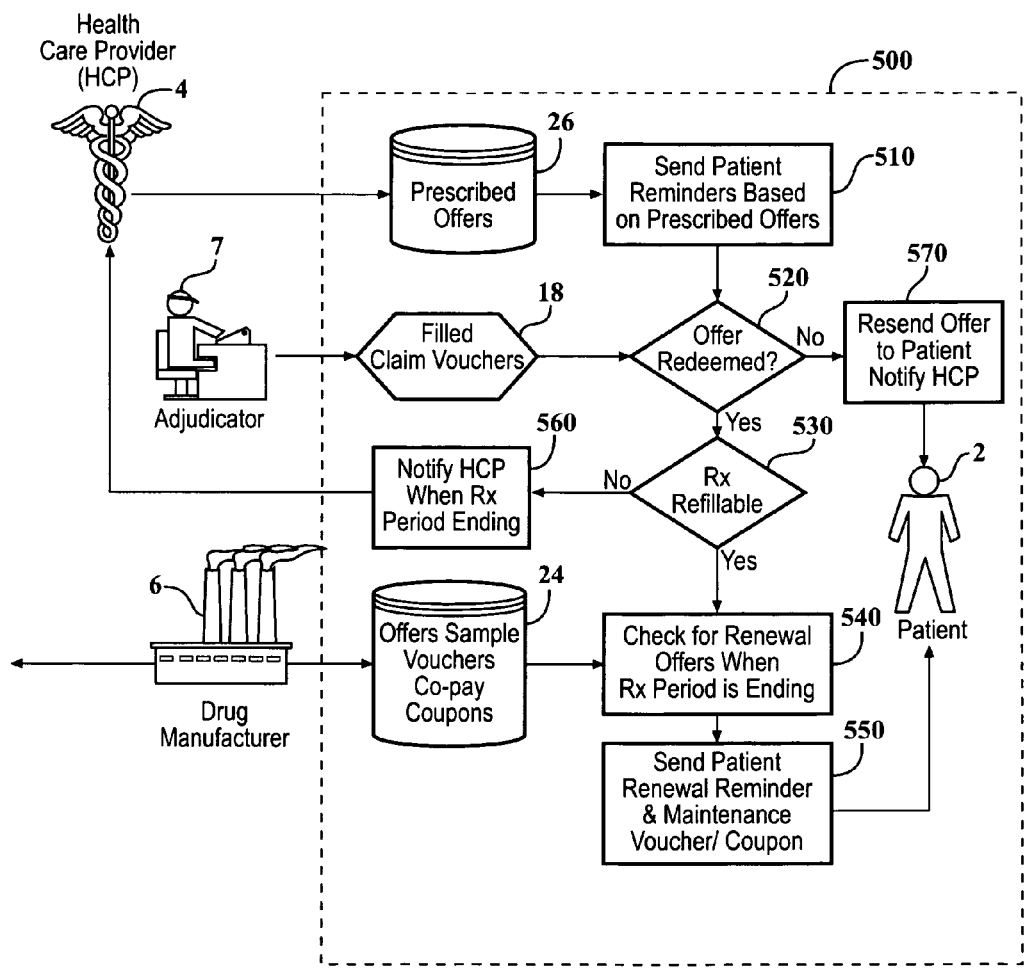
FIG. 5 is a high level diagram illustrating an exemplary process flow for usage of the system to automate the patient follow-up procedure with co-pay coupons and savings vouchers for prescriptions within a health care environment according to various aspects of the present disclosure.

FIG. 5 is a process flow diagram illustrating a method for automating the follow-up procedure of the discount offers made using the virtual sample cabinet system 100. In particular, FIG. 5 implements the follow-up method primarily using the software modules within the automated patient follow-up assistant subsystem 150 of the overall VSC system 100. The patient follow-up procedures 500 are designed to improve patient compliance and prescription maintenance. This is a main goal for drug manufacturers 6 and this means to retain customers is a main reason for the offer of drug prescription incentives.

As seen in the prescribing process 400 the HCP 4 creates the prescribed offer database 26. On a daily basis the automated patient follow-up assistant subsystem 150 runs processes which search the databases within the VSC data center 20 and performs a send patient reminders based on prescribed offers process 510 which communicates electronically via email or even via conventional mail. The patient 2 is thereby sent a reminder that their prescription is near expiring or running out if they have been following the prescribed dosages. The offer redemption process 520 checks the filled claim vouchers database 18 created by the insurance adjudicators 7 and determines the response of the patient 2 to said reminders. If the offer has not been redeemed, a resend offer to patient and notify HCP process 570 is executed. Greater encouragement or even enticements can be made in this process to induce a hesitating patient 2 to maintain the proper level of their treatment process. If the last discount offer has been redeemed, the next step in the follow-up process 500 is to perform a check with prescription is refillable process 530. If not, it is important to perform a notify HCP when Rx period is ending process 560, whereby the HCP 4 has the monitoring information necessary to decide how to follow-up with their patient 2. Depending on their perceived urgency, the HCP 4 can either contact the patient 2 immediately or wait until their next scheduled appointment.

If the prescription is refillable, a check for renewal offers when Rx period is ending process 540 is executed and by use of the offers database 24 which has been kept current by the drug manufacturer 6 this procedure can locate the appropriate offers to send the patient 2 to maximize their continued savings. These savings are then communicated at the appropriate time using a send patient renewal reminder and maintenance voucher/coupon process 550. The virtual sample cabinet system 100 by virtue of providing the subsystem automated patient follow-up assistant 150 can support the follow-up process 500 and ensure that patient compliance to their prescription drug regimen is improved.

Figure 6:
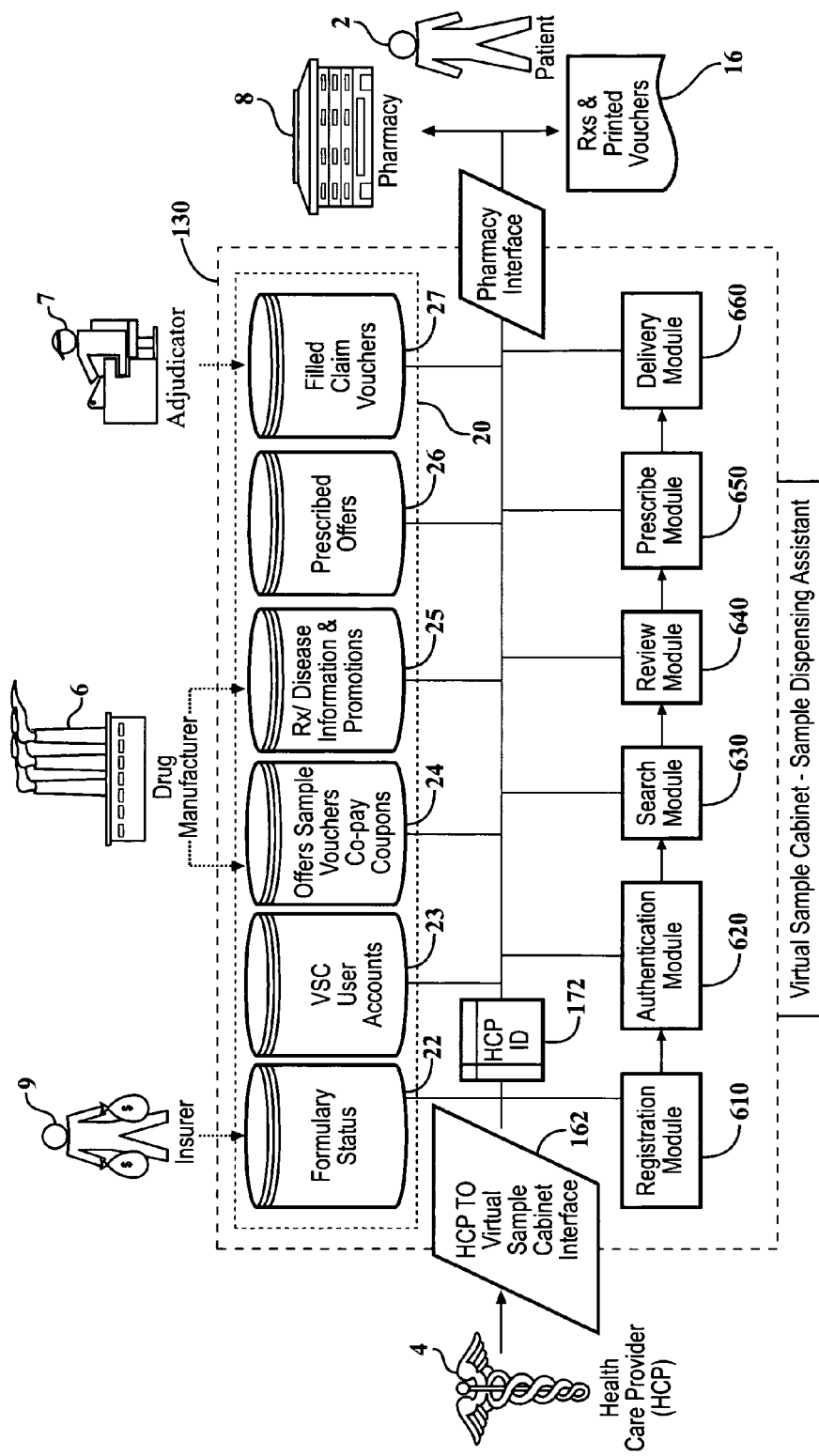
FIG. 6 is a diagram detailing the subsystem which performs the methods of a sample dispensing assistant as part of the virtual sample cabinet for prescription drugs according to various aspects of the present disclosure.

The main components or subsystems of the VSC system 100 are shown in FIG. 1. FIG. 6 details the subsystem, which performs the methods of a sample dispensing assistant 130, as part of the virtual sample cabinet 100 for prescription drugs according to various aspects of the present disclosure. As shown in FIG. 6, the individual databases within the VSC data center 20 are accessed by the other software modules, and complete the ability of the sample dispensing assistant 130 to complete the flow of the procedures detailed in FIG. 4.

Also shown in FIG. 6, the HCP 4 communicates with the sample dispensing assistant 130 using the HCP to virtual sample cabinet interface 162. A registration module 610 serves to allow the HCP 4 to uniquely verify their identity and create an entry in the VSC user account database 23. A unique identification number 172 is generated during registration for each HCP. This unique id 172 is used by the HCP during future logins to the VSC system 100. An authentication module 620 when provided with the unique identification information allows the HCP 4 to have access to perform the other system functions.

After HCP 4 login, the search module 630 assists the HCP in seaching the offers database 24 to determine which prescription drugs are suitable for the patient 2. A review. module 640 assists the HCP 2 in the final selection so that the drug recommended for the patient is covered by the patients insurance or is as shown by the entries in the formulary status database 22. Further review by the HCP of the corresponding entries in the disease Rx information and promotions database 25 affords the information which is useful in discussion with the patient 2 and provides takeaway literature to assist the patient in better understanding their own drug treatment.

A prescribe module 650 then provides the ability to the HCP 4 to make the final drug selection and write the necessary prescription including drug, dosage, frequency, and time course. A delivery module 660 permits the patient 2 to decide how they would like to obtain their prescription. The HCP 4 can use the delivery module 460 to generate hard copies or Rxs and printed vouchers 16 for hand delivery by the patient 2 to any pharmacy 8 that decide to engage. Alternatively the delivery module 460 can be used to communicate with the pharmacy interface module 470, which has access to the stored information necessary to electronically transmit the prescription and voucher information to the pharmacy 8 of patient 2 selection.

Figure 7:
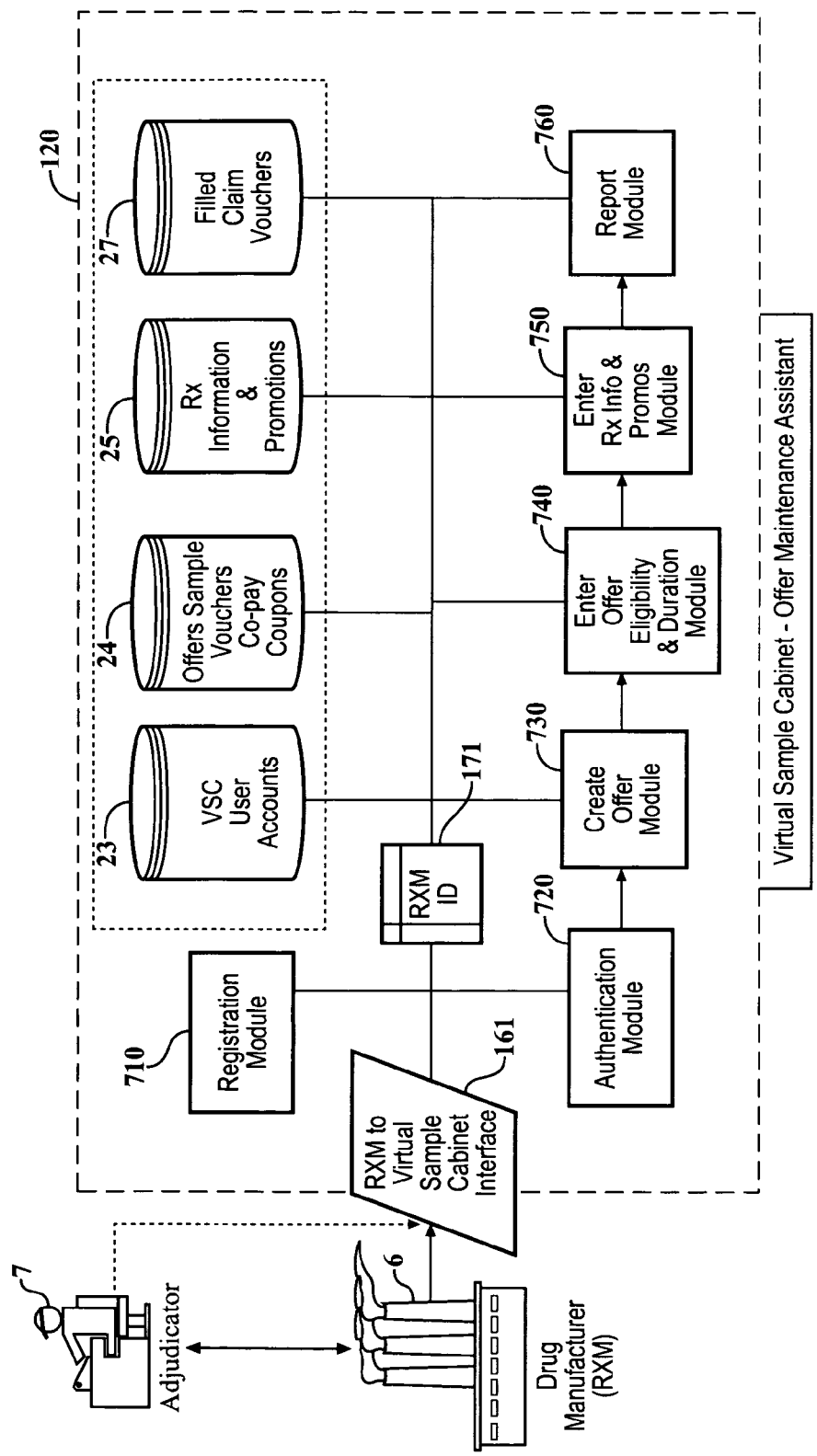
FIG. 7 is a diagram detailing the subsystem which performs the methods of an offer maintenance assistant as part of the virtual sample cabinet for prescription drugs according to various aspects of the present disclosure.

FIG. 7 details the subsystem, which performs the methods of an offer maintenance assistant 120 as part of the virtual sample cabinet 100 for prescription drugs according to various aspects of the present disclosure. As shown in FIG. 7, the individual databases within the VSC data center 20 are accessed by the other software modules, and complete the ability of the offer maintenance assistant 120 to complete the flow of the procedures detailed in FIG. 5.

It is the drug manufacturers 6 that initiate the promotion offers for their own drugs. However they may allow a third party such as insurance adjudicators 7 or their marketing agency to create offers on their behalf. The entrusted party goes through the system registration process similar to that shown in FIG. 6 above. The drug manufacturer (RXM) 6 communicates with the VSC system 100 using the RXM to virtual sample cabinet interface 161. A registration module 720 serves to allow the RXM 6 to uniquely verify their identity and create an entry in the VSC user account database 23. A unique identification number 171 is generated during registration for each RXM. This unique id 171 is used by the RXM or their proxy during future logins to the VSC system 100. An authentication module 720 when provided with the unique identification information allows the RXM 6 to have access to perform the other system functions.

After RXM 6 login, and authentication, the initialize offer module 730 assists the RXM in creating the details of the offer on each drug for which incentive program is desired. The RXM 6 also designs any number or timings of the follow-on offers using this module. A enter offer location and schedule module 740 assists the RXM 6 with the limiting the range of the offers. These limitations may be set for example based on physical locations, specific groups of insurers, specific demographics of patients among other criterion. This allows the RXM 6 to better target their marketing and to refine their offers.

The enter Rx info and promos module 750 allows the RXM 6 to provide the supplemental medical and marketing information about the drug and associated medical conditions that it is recommended to treat. This is key step where the package of literature to be sent to remind and encourage patient 4 of the imminent prescription expiration and to improve compliance drug is configured.

A report module 760 then provides the ability to the RXM 6 to make perform the queries and generate the summary reports to track how their drug incentive programs are progressing. Based on the reports coming out from this module the RXM 6 may go back to the initialize offer module 730 or enter offer location and schedule module 740 to make adjustments to the ongoing promotional programs.

FIG. 8 summarizes the essential steps used by prior art systems in performing management of physical drug samples and permits comparison of these steps with those supported by the virtual sample cabinet system 100. The symmetric side-by-side arrangement of the process flows in FIG. 8 allows analysis of their essential differences and improvements of the present disclosure. A major contrast between flow in the prior art and the VSC system 100 is seen in the reduction from twelve to seven processes. FIG. 8 makes it evident that five major processes are able to be eliminated by employ of the efficiencies introduced by the methods of this disclosure. This figure reiterates the contrast that as shown in the comparison between FIG. 3 and FIG. 4 the financial burden upon the drug manufacturers to create the physical samples and distribute them in prior art are obviated by the present invention.

Figure 9:
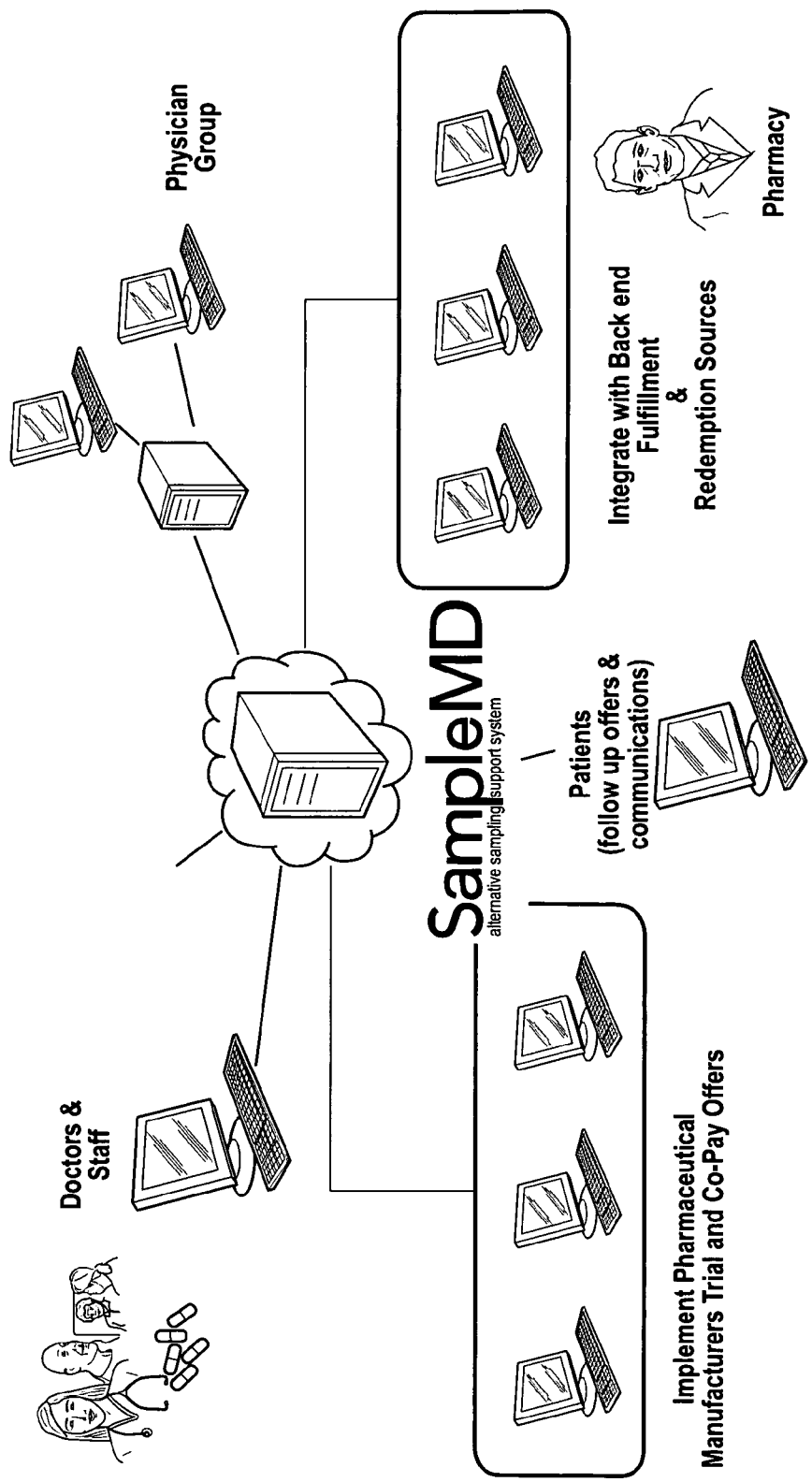
FIG. 9 is a block diagram illustrating a system to enhance distribution and tracking of prescription drug samples and savings coupons for prescriptions via the Internet according to various aspects of the present disclosure.

FIG. 9 shows the flow of communications between various users of an exemplary system, called SampleMD, for the disclosed methods. SampleMD serves as the portal and integrator to all key parties and all necessary functions. Various embodiments of the method may not include all of the participants shown in this figure, or alternative system layouts may be developed which provide special interfaces or features for certain participants. But the general software modules can be adapted to accommodate for these special features. As shown in FIG. 9, the central SampleMD server is accessed though the Internet by individual doctors and staff, physicians at physician groups through a local server, and patients on their home computers for follow-up offers and customer communications. As shown in FIG. 9 pharmacies connect to the central system server to integrate with backend fulfillment and redemption sources. Finally drug manufacturers connect to the computer framework in order to implement their pharmaceutical trial and co-pay offers.

FIG. 10 shows a representative screen layout for entry of information for the creator of a new health care provider as part of the download and registration setup of the desktop software for the representative embodiment or SampleMD system. The health care provider goes to a website such as www.samplemd.com to download their specific search "widget" onto their desktop by registering their information as shown in the figure. In alternative embodiments the search widget can also be uploaded onto the website ore e-prescribing portal (through HTML code, etc.)

After completion of the download step, the unique tagged sample search widget is instantly downloaded on the health care providers desktop. As shown in FIG. 11, the provider simply types in their name and state license number or DEA number and selects their state in order to complete the registration process on their desktop computer. This utility then allows for searches of available hosted prescription free sample vouchers and co-pay savings offers from multiple brands and manufacturers.

As shown in FIG. 12*a*, upon completion of download and registration, the provider simply types in the product name to trigger "drop down" of available results for each searched product (or alternatives within the same therapeutic class of drugs). As shown in FIG. 12*b*, providers can also access insurance drug information to review specific drug co-pays and formulary status, as well as prescribing information for drugs.

Figures 13A, 13B:
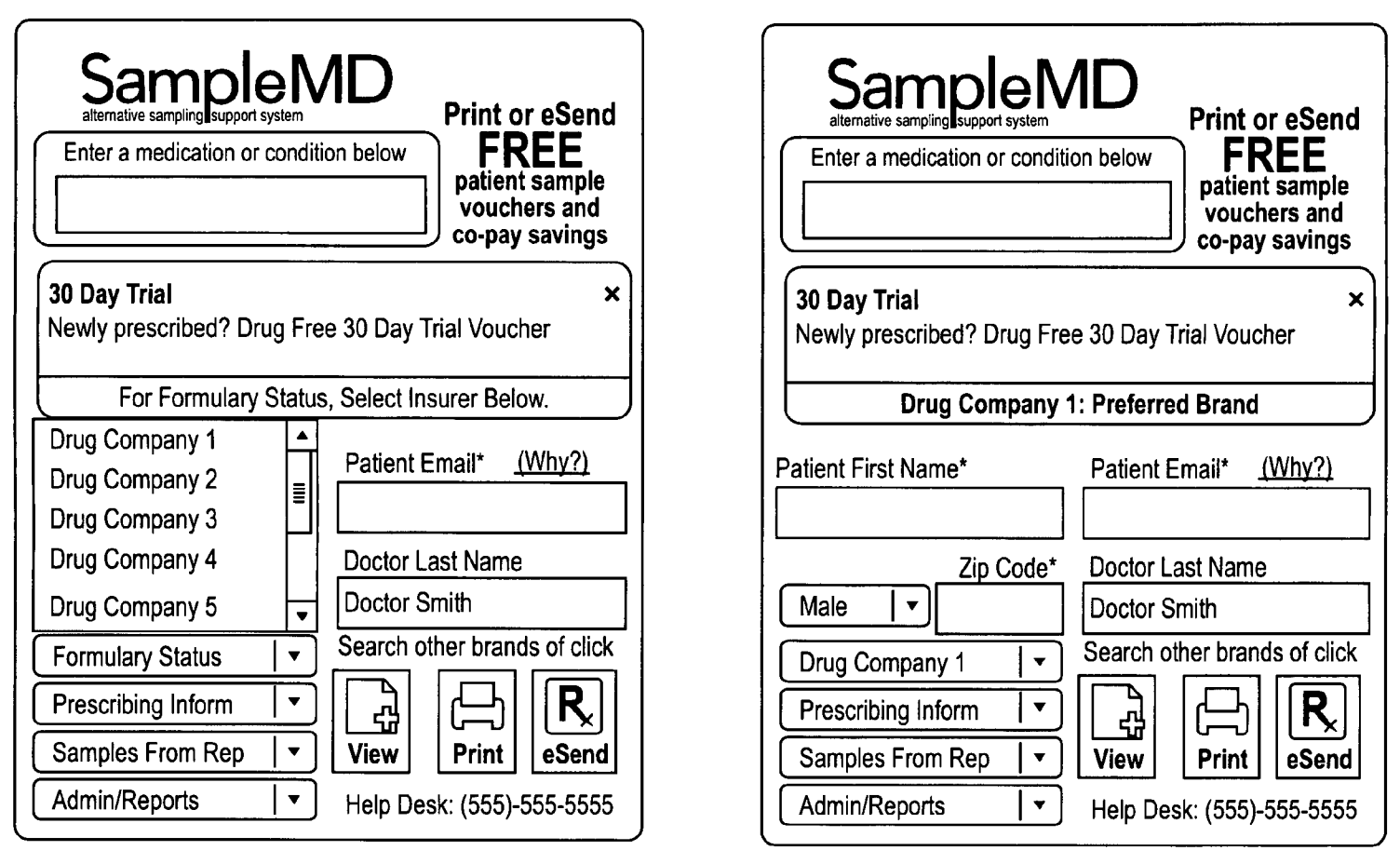

As shown in FIG. 13, the desired offers are reviewed and selected. From there the basic patient information is inputted, as well as ability to look up their insurance plan's coverage of each selected drug offer. Each free voucher or savings coupon is assigned a set of patient ID numbers to track its redemption and can be printed or e-sent for redemption within an extensive national network of pharmacies. In alternative embodiments, the provider can e-send the coupon to a selected pharmacy along with the generated prescription (see also FIG. 14). In yet alternative embodiments, the system can automate emails of additional refill offers available for a product to promote compliance to long term therapy. As shown in FIG. 13, the provider presses the appropriate menu selection to choose between e-send or print of the discount offer. In order to do the adjudication, the VSC server receives key data in real-time that is assigned to that specific patient information. This may include member/patient number, group number and BIN. This information allows central tracking and reporting on the specific patient fulfillment of this particular and all future offers.

Figure 15:
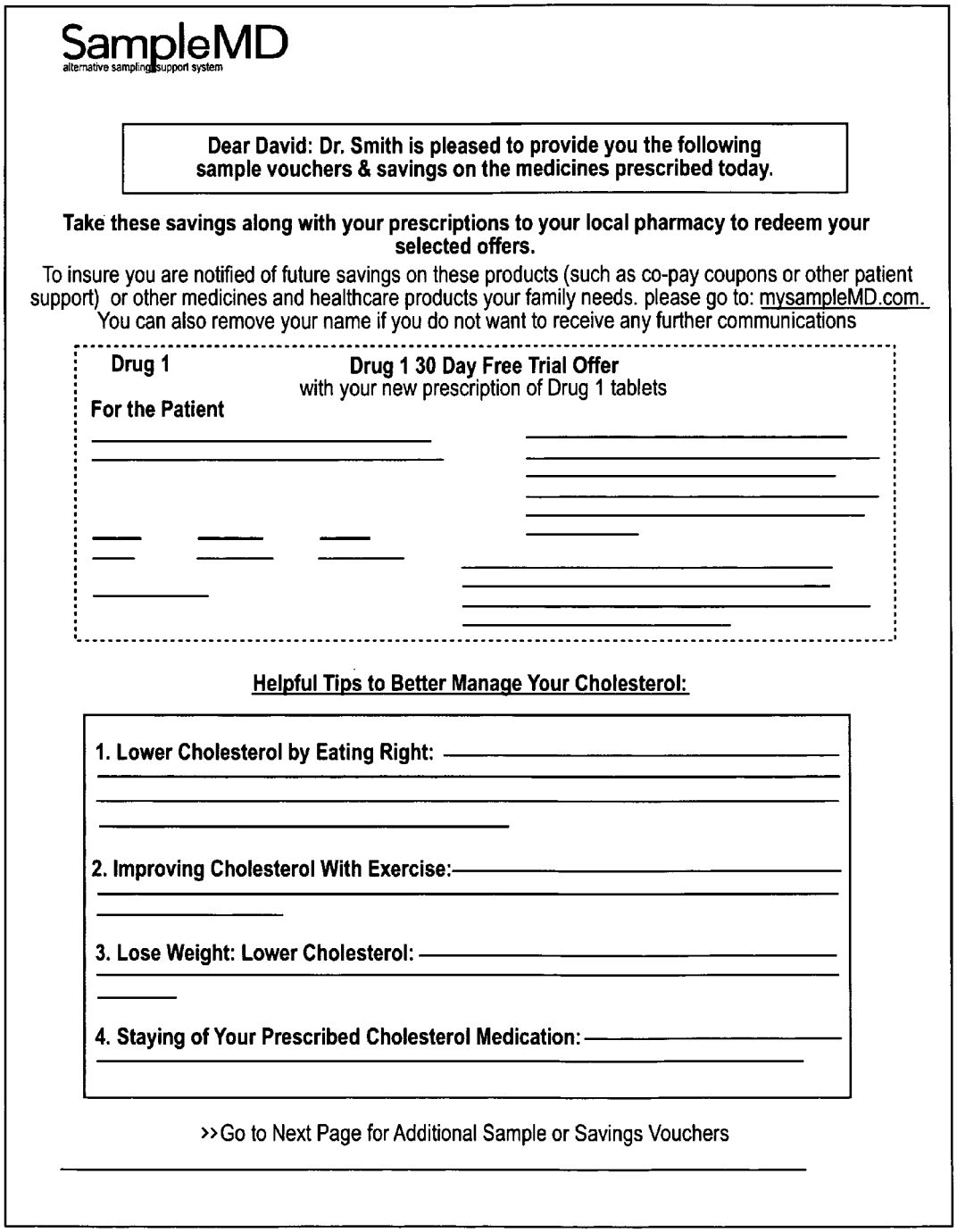
FIG. 15 shows a representative print out of the discount offer generated by the health care provider as part of the voucher generation by the virtual sample cabinet system in accordance with a SampleMD embodiment of the present invention.

FIG. 15 shows a representative print out of the discount offer generated by the health care provider as part of the voucher generation by the VSC system. Print of offers is dynamically automated with providers and patient's names, the offer patient and pharmacy information and the necessary information to print or e-send for redemption of the voucher or coupon through the correlating company. Patients will also automatically receive future savings on the selected offers. As shown in the FIG. 15, in other embodiments, helpful tips to manage the product condition are also included in the printouts.

Figure 16:
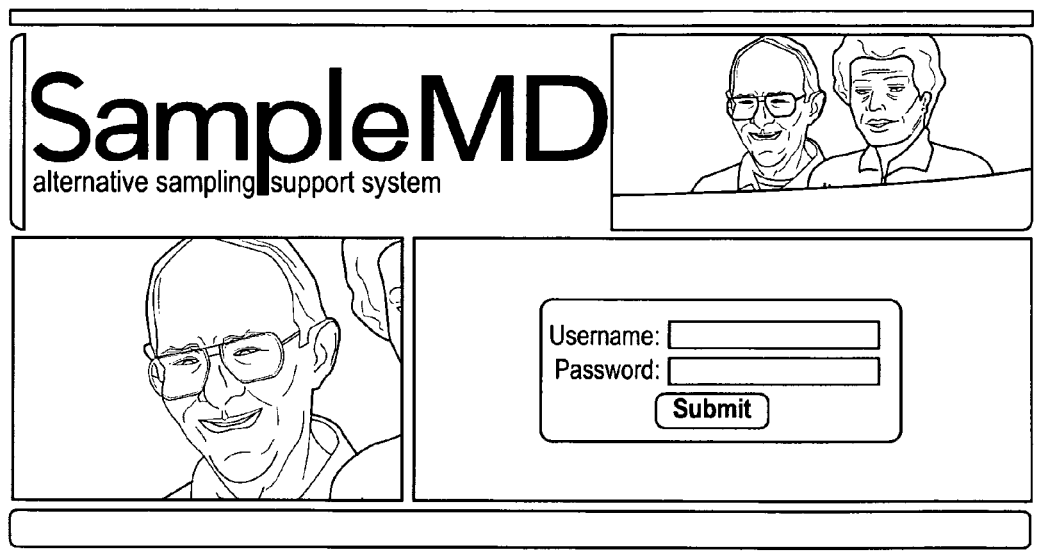
FIG. 16 shows a representative screen layout for entry of login information for creators of drug incentive programs as part of the virtual sample cabinet system in accordance with a SampleMD embodiment of the present invention.

FIG. 16 shows a representative screen layout for entry of login information for creators of drug incentive programs as part of the VSC system. The functionality then accessible allows online login of staff to build, manage and report offers by utilization of doctors, their affiliate group and geographical area. Additionally it also allows information on insurance drug formulary information and prescribing information through an integrated database. Alternative embodiments allow the client access at various levels of information pertaining to their product or group.

Figure 17:
FIG. 17 shows a representative screen layout for entry of information by the drug manufacturer of voucher or coupon information as part of the creation of a new incentive for the virtual sample cabinet system in accordance with a SampleMD embodiment of the present invention.

FIG. 17 shows representative screen layouts for entry of information by the drug manufacturer to create a sample voucher or co-pay coupon incentive within the VSC system. The VSC system allows the manufacturer to dynamically generate and promote printable or electronically transferred vouchers or coupons tied and identified to patient, doctor, affiliation and manufacturer that allows for redemption processing data to be pulled and entered on coupon for redemption and tracking within a large network of pharmacies. The screens show offer development, management, and reporting.

Figure 18A:
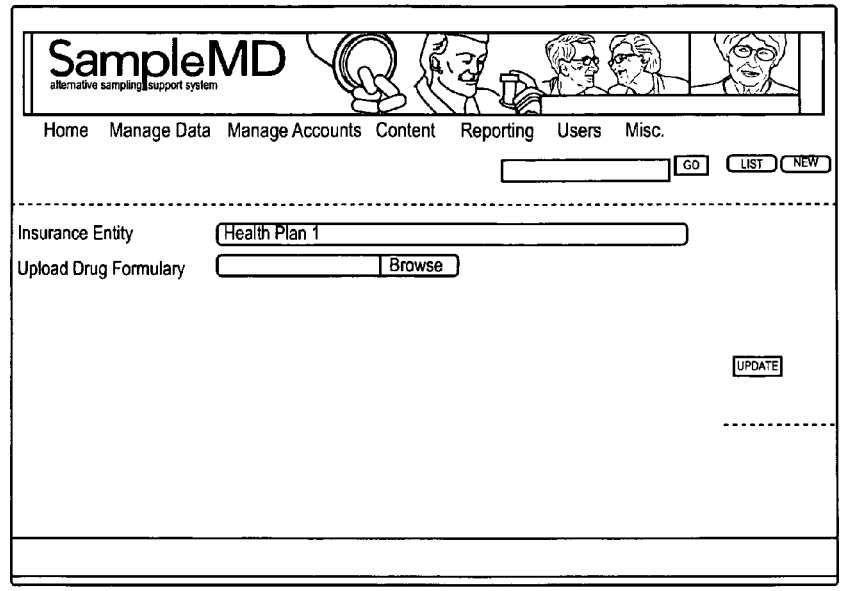
FIGS. 18a and 18b shows several representative screen layouts for creation of drug formulary information by the HMO and insurance companies as part of the database creations utilized by the virtual sample cabinet system in accordance with a SampleMD embodiment of the present invention.
Figure 18B:

FIGS. 18*a* and 18*b* shows several representative screen layouts for creation of drug formulary information by the HMO and insurance companies as part of the database creations utilized by the VSC system. In this embodiment, as shown in FIG. 18, the database of Leading HMO/Insurance companies is created that upon selection delivers "formulary coverage status of product within search results. For further information, the user can click on the Insurer link to open up full drug coverage information.

Figure 19B:
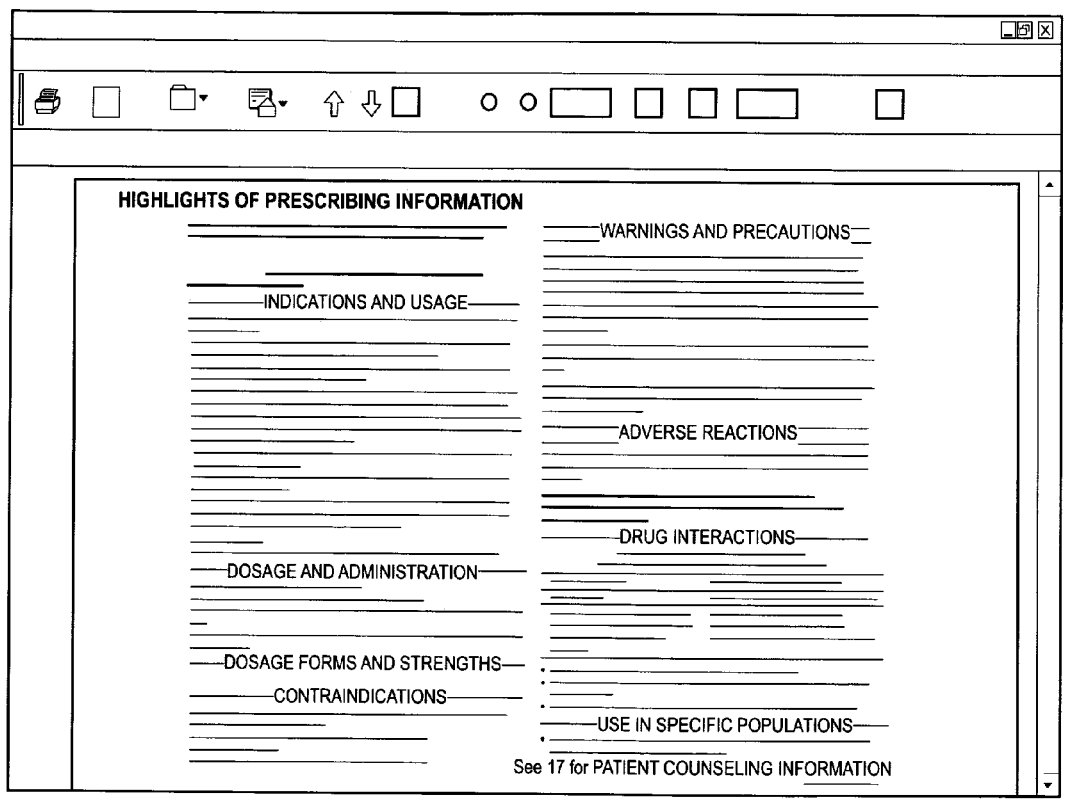

FIGS. 19*a* and 19*b* shows several representative screen layouts for creation of drug prescribing information by the drug manufacturer companies as part of the database creations utilized by the VSC system. As shown in FIG. 19 the drug manufacturer can create the prescribing information reference or the database of product prescribing information for doctor or care providers to centrally access.

Figure 20:
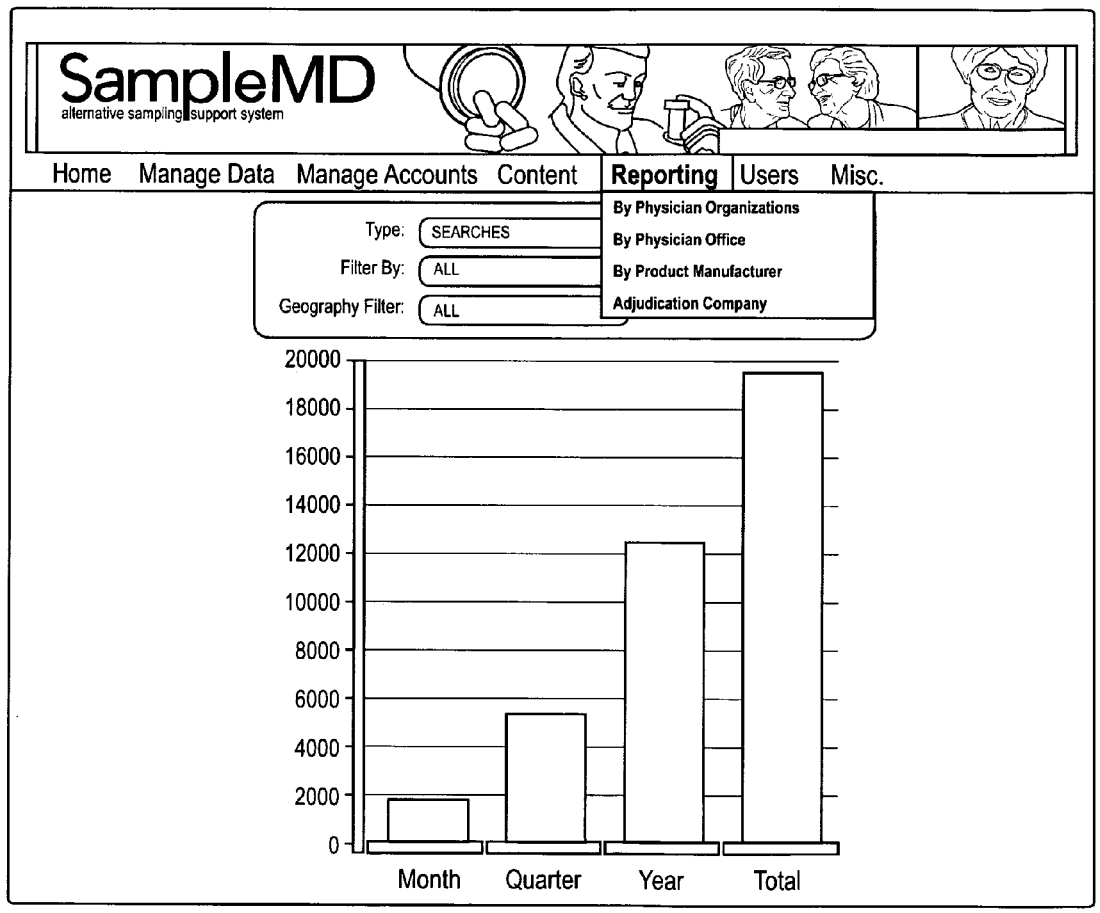
FIG. 20 shows a representative screen layout for display of information by the drug manufacturer of usage of vouchers or coupons as part of the analysis of an incentive by the virtual sample cabinet system in accordance with a SampleMD embodiment of the present invention.

FIG. 20 shows several representative screen layouts for display of information by the drug manufacturer of usage of vouchers or coupons as part of the analysis of an incentive by the representative SampleMD system. As seen in FIG. 20, the user can generate utilization reports by product, affiliate group, doctor, and sales representative. Redemption data is pulled from data from the adjudicating company to generate the desired utilization reports.

Figure 21A:
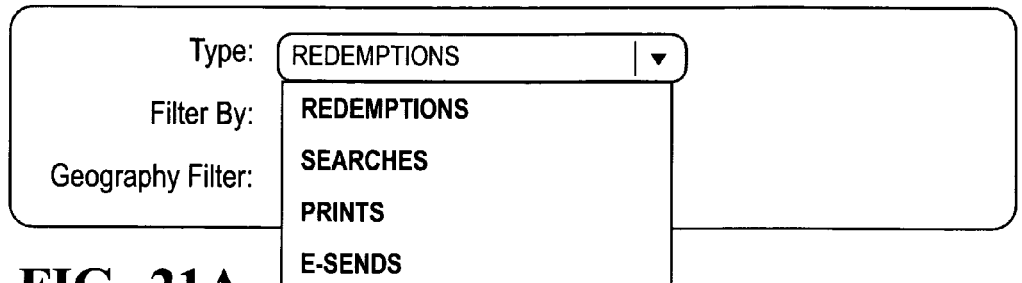
FIGS. 21a, 21b and 21c shows several representative screen layouts for menu based generation of reports and graphs by the drug manufacturer or adjudication companies, physician offices, and physician organizations as part of the reporting features supported by the virtual sample cabinet system in accordance with a SampleMD embodiment of the present invention.
Figure 21B:
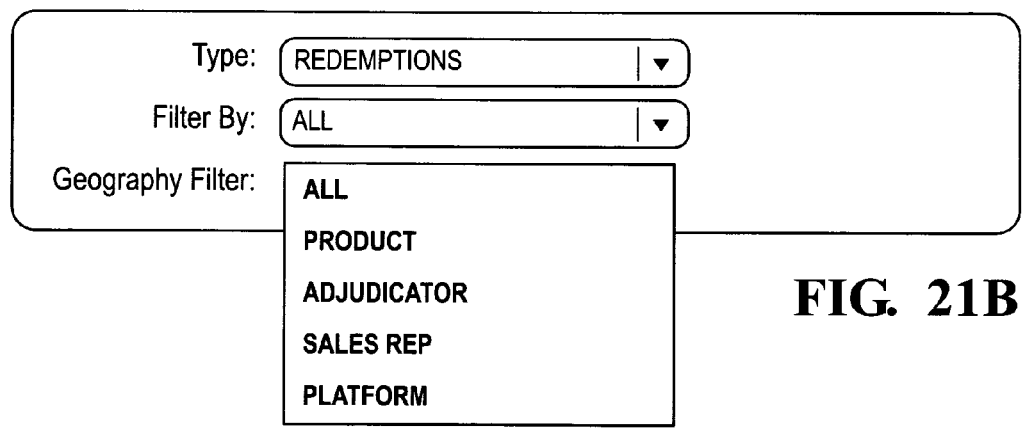
Figure 21C:
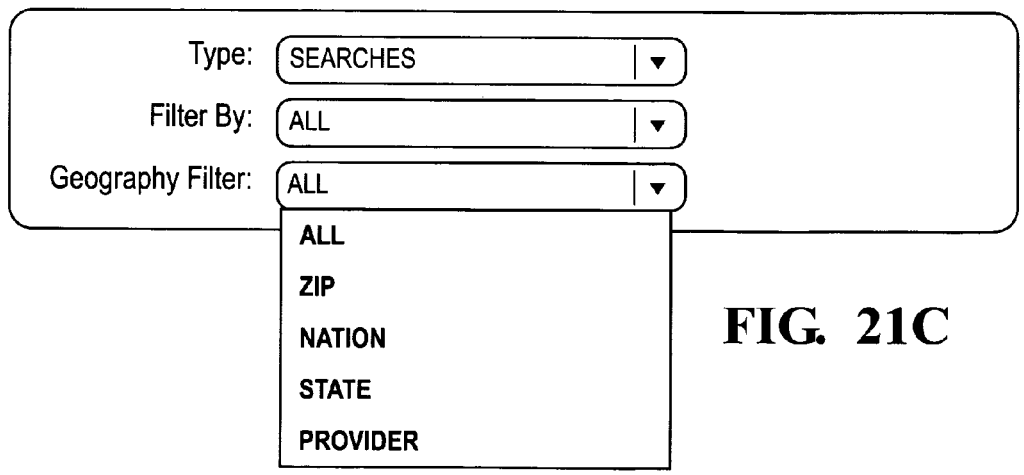

FIG. 21 shows the various data sorts that can be viewed by approved viewers based on login rights, including Drug Manufacturers, affiliate health systems, HCPs, Voucher Adjudicating Vendors, Sales Reps and SampleMD Adminstrators, Data is updated in real time within the VSC via each action recorded.

Those skilled in the art can now appreciate from the foregoing description that the broad teachings of the present disclosure can be implemented in a variety of forms. Therefore, while this disclosure has been described in connection with particular examples thereof, the true scope of the disclosure should not be so limited since other modifications will become apparent to the skilled practitioner upon a study of the drawings, specification, and the following claims.

What is claimed is:

1. A method of facilitating the promotion of prescription drugs by offering price incentives, the method comprising:
    a) collecting promotional offers by various companies set by those companies and qualification parameters for various drugs sold by them;
    (b) electronically storing and updating said collected promotional offers and qualification parameters in a central drug incentive database and system;
    (c) programming a software module to allow remote access to the central drug incentive database and system via the internet;
    (d) registering a healthcare providers to permit their use of the software module and thereby to enable
    (e) enabling access to said central drug incentive database and system by said software module via the internet by a using registered healthcare provider to inform the provide information to the using registered healthcare provider of available offers on particular prescription drugs when prescribing a drug being prescribed for the condition of a patient being treated by the using health care provider based on information on the patient condition and the registered healthcare provider electronically provided to the software module by the healthcare provider;
    (f) enabling electronic selection using said software module by the using healthcare provider of one or more incentives available for the drug being prescribed for the patient and condition being treated by the using healthcare provider based on an electronic check of the central drug incentive database as well as the formulary status data for the particular drug being prescribed, and alternatives to the particular drug being prescribed within a class of drug, and as reflected by the information provided by the using healthcare provider; concerning the particular healthcare provider, and the patient, and the patient condition to be treated with the prescribed drug;
    (g) enabling the using healthcare provider to electronically select the method of delivery to present the selected incentive to a selected pharmacy;
    (h) enabling the optional printing by the health care provider of a coupon identifying a selected incentive or alternatively the electronic transmission of a selected incentive to said selected pharmacy with required claim information for billing of the manufacturer by the selected pharmacy;
    (i) enrolling the patient to electronically receive refill reminders for available on-going discounts and other educational support on the allocated drugs;
    (j) capturing the information about the incentive selection and orders fulfilled by said pharmacies using said software module;
    (k) entering the information about the incentive selection and order fulfillments into the central drug incentive database; and
    (i) electronically generating reports summarizing the selection, use, and overall effectiveness of offered incentives from data collected in said central drug incentive database by said system and electronically transmitting said reports to the manufacturer of the drug; thereby facilitating the processes of informing the health care provider of the availability and details of drug incentives, the selection and tracking of incentives such as prescription drug sample vouchers, co-pay coupons, and free trials as well as to efficiently enable patients to obtain the benefits of such incentives and to inform drug companies of the effectiveness of such incentives.

2. The method of facilitating the promotion of prescription drugs according to claim 1 wherein said software module is sent directly to a computer mobile device or other web-based platform used by the health care provider.

* * * * *

UNITED STATES PATENT AND TRADEMARK OFFICE
CERTIFICATE OF CORRECTION

| | | |
|---|---|---|
| PATENT NO. | : 8,341,015 B2 | Page 1 of 1 |
| APPLICATION NO. | : 12/655558 | |
| DATED | : December 25, 2012 | |
| INVENTOR(S) | : David A. Harrell | |

It is certified that error appears in the above-identified patent and that said Letters Patent is hereby corrected as shown below:

In the Claims:

Column 19:

Line 21: delete "a"

Line 22: delete "and thereby to enable" insert --;--

Line 25: delete "inform the"

Line 28: delete "when prescribing a drug"

Line 37: delete "and"

Column 20:

Line 2: delete "and"

Line 3: delete ";" after "provider"

Line 24: delete "(i)" insert --(l)--

Signed and Sealed this
Twelfth Day of November, 2013

Teresa Stanek Rea
*Deputy Director of the United States Patent and Trademark Office*